(12) United States Patent
Komiya et al.

(10) Patent No.: US 10,178,999 B2
(45) Date of Patent: Jan. 15, 2019

(54) ENERGY TREATMENT UNIT, ENERGY TREATMENT INSTRUMENT AND ENERGY TREATMENT SYSTEM

(71) Applicant: OLYMPUS CORPORATION, Hachioji-shi, Tokyo (JP)

(72) Inventors: Mizuki Komiya, Hachioji (JP); Kazunori Taniguchi, Hamburg (DE)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/383,220

(22) Filed: Dec. 19, 2016

(65) Prior Publication Data

US 2017/0095262 A1    Apr. 6, 2017

Related U.S. Application Data

(63) Continuation of application No. PCT/JP2015/062864, filed on Apr. 28, 2015.

(30) Foreign Application Priority Data

Jun. 19, 2014  (JP) .................................. 2014-126626

(51) Int. Cl.
    *A61B 17/22*  (2006.01)
    *A61B 18/00*  (2006.01)
    *A61B 18/12*  (2006.01)

(52) U.S. Cl.
    CPC .... *A61B 17/2202* (2013.01); *A61B 17/22004* (2013.01); *A61B 18/00* (2013.01); *A61B 18/12* (2013.01)

(58) Field of Classification Search
    CPC ..... A61B 18/00; A61B 18/12; A61B 17/2202; A61B 17/22004
    See application file for complete search history.

(56) References Cited

U.S. PATENT DOCUMENTS 3,805,787 A    4/1974  Banko
5,100,424 A *  3/1992  Jang .......................... A61B 8/12
                                                    600/439

(Continued)

FOREIGN PATENT DOCUMENTS

CN    103118603 A    5/2013
DE      4102090 A1   7/1992

(Continued)

OTHER PUBLICATIONS

Dec. 29, 2016 Translation of International Preliminary Report on Patentability issued in PCT/JP2015/062864.

(Continued)

*Primary Examiner* — Peter Luong
(74) *Attorney, Agent, or Firm* — Oliff PLC

(57) ABSTRACT

A liquid feed conduit and a suction conduit extends in a hollow portion from a probe proximal portion direction to a probe distal portion direction in an inside of a probe, and an ejection port of the liquid feed conduit and a suction port of the suction conduit are located in the hollow portion. A collision surface is provided in the probe to be opposed to at least a part of the ejection port, and the collision surface is located on the probe distal portion direction side with respect to the suction port and the ejection port. At least part of a liquid ejected from the ejection port collides with the collision surface in the hollow portion.

21 Claims, 19 Drawing Sheets

(56) References Cited

U.S. PATENT DOCUMENTS

| | | | |
|---|---|---|---|
| 5,163,433 A | 11/1992 | Kagawa et al. | |
| 2002/0077550 A1* | 6/2002 | Rabiner | A61B 17/22012 |
| | | | 600/439 |
| 2007/0162050 A1 | 7/2007 | Sartor | |
| 2012/0253371 A1 | 10/2012 | Ross et al. | |
| 2013/0190790 A1 | 7/2013 | Akagane et al. | |
| 2013/0324917 A1* | 12/2013 | Akagane | A61B 17/320092 |
| | | | 604/35 |

FOREIGN PATENT DOCUMENTS

| | | |
|---|---|---|
| JP | 4-361743 B2 | 11/2009 |
| WO | 2012/114977 A1 | 8/2012 |
| WO | 2012/124653 A1 | 9/2012 |

OTHER PUBLICATIONS

Jul. 12, 2016 Office Action issued in Japanese Patent Application No. 2016-528919.
Jun. 30, 2015 International Search Report issued in International Patent Application No. PCT/JP2015/062864.
Feb. 5, 2018 Extended European Search Report issued in European Patent Application No. 15810613.8.
Jun. 1, 2018 Office Action issued in Chinese Patent Application No. 201580033073.3.

\* cited by examiner

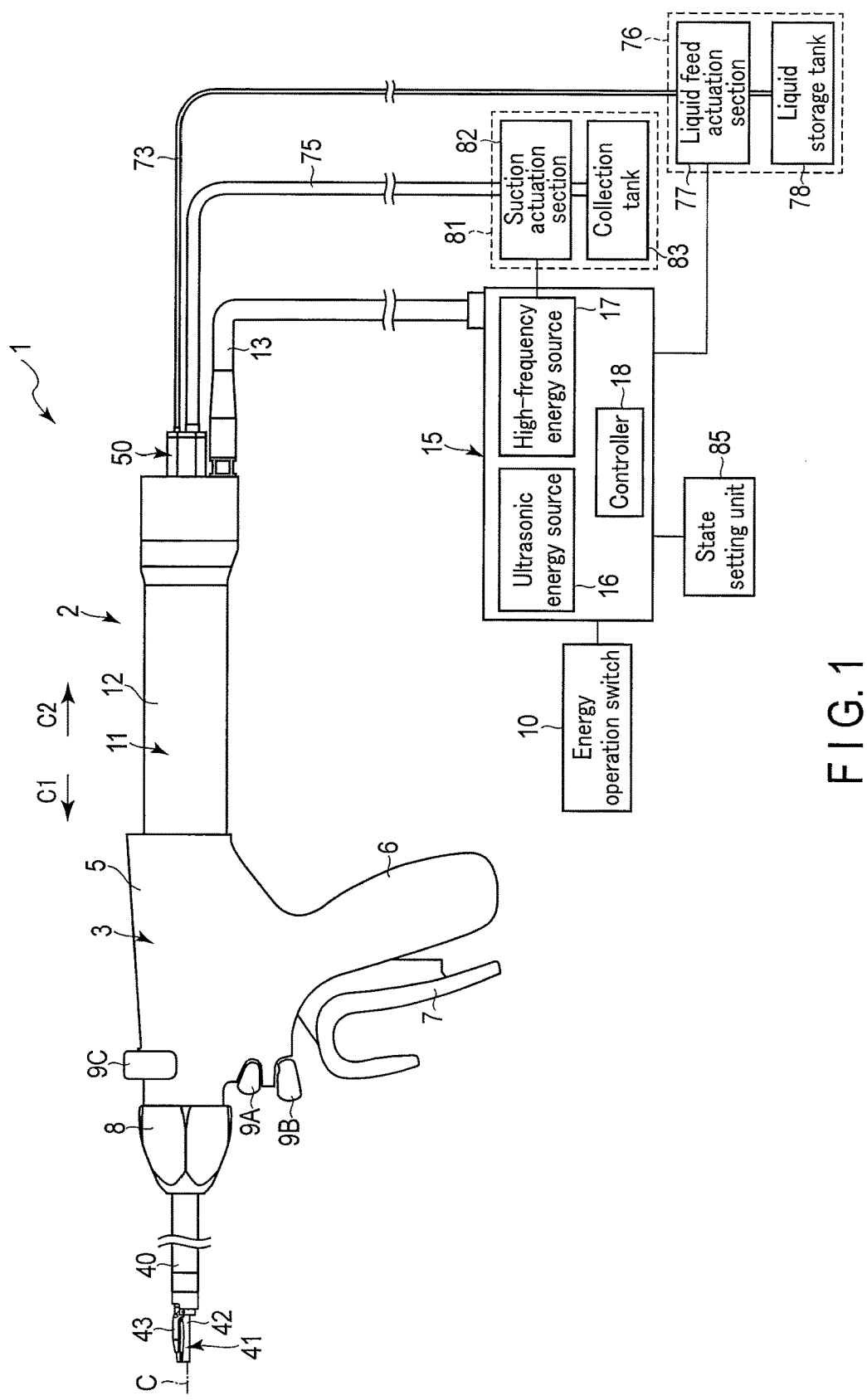
F I G. 1

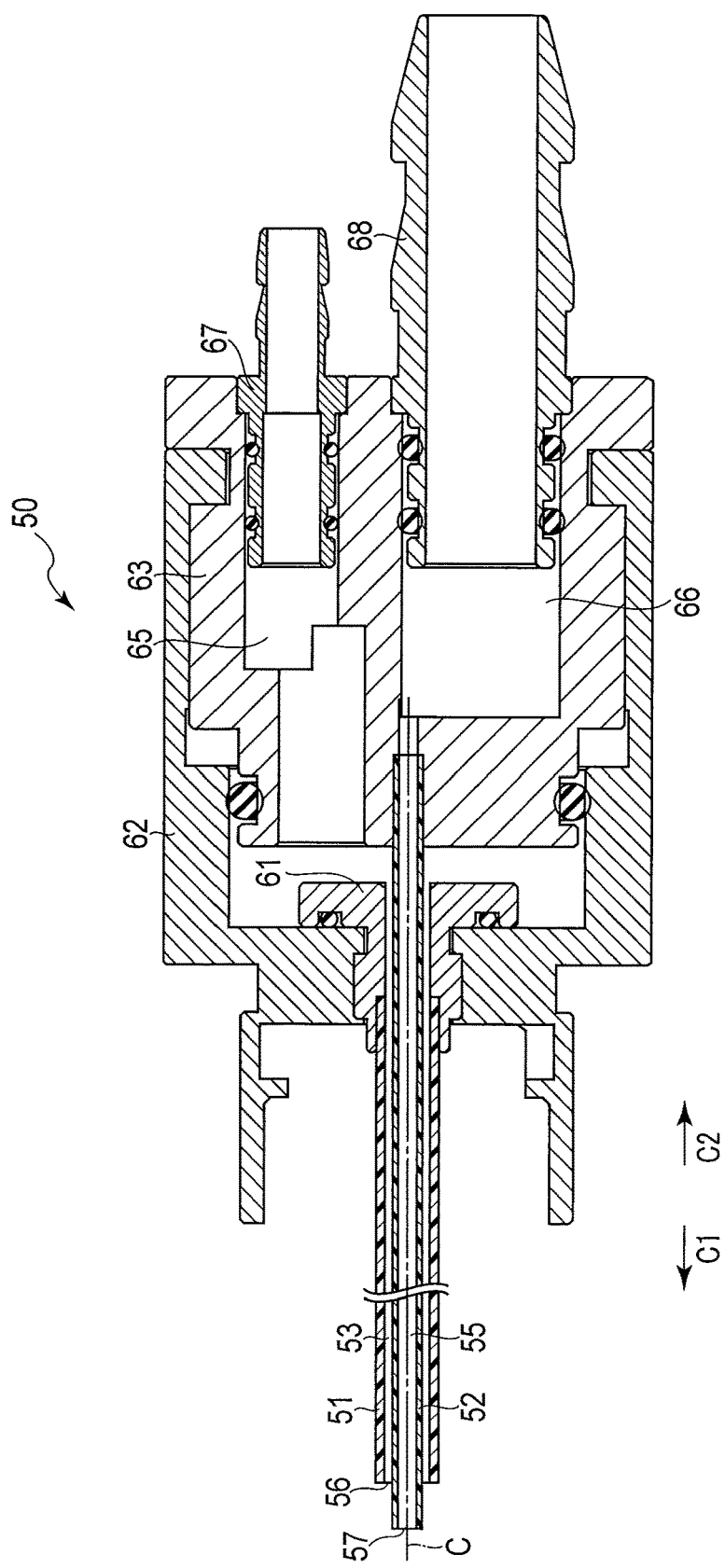
F I G. 5

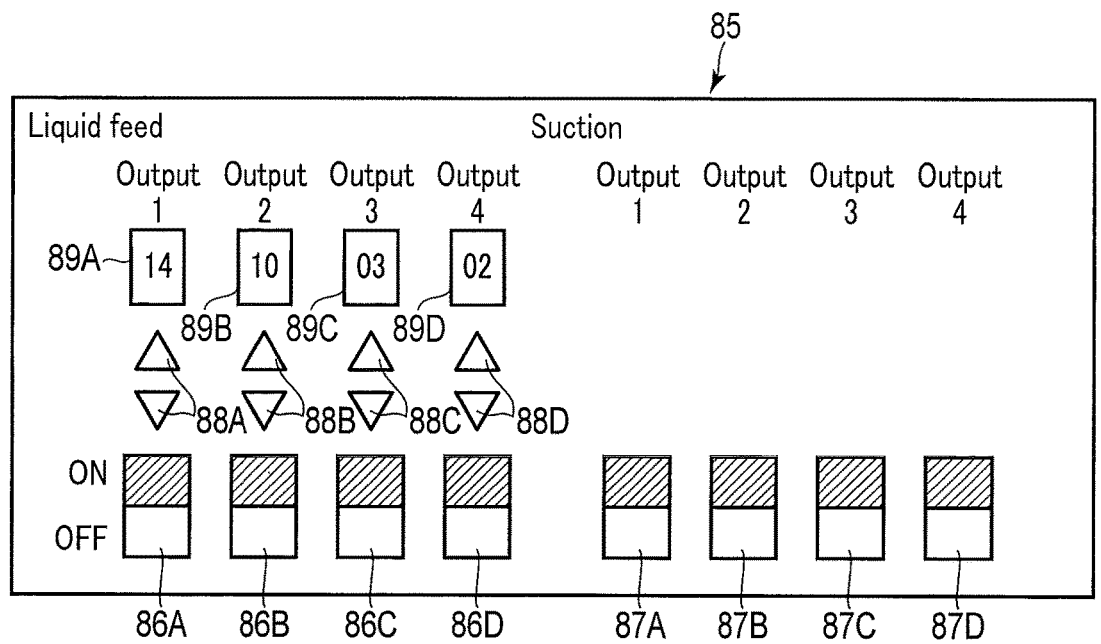
F I G. 8
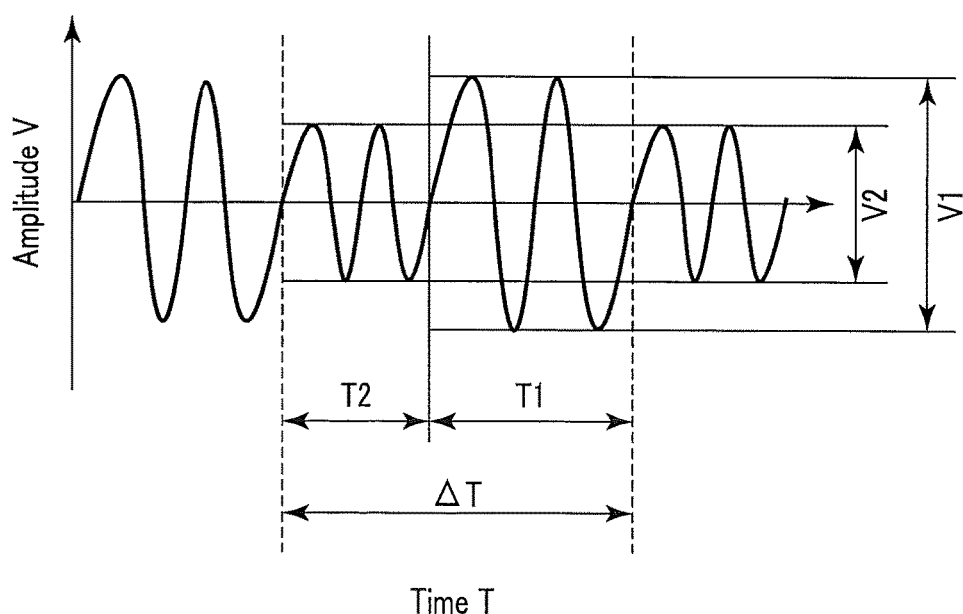
F I G. 9

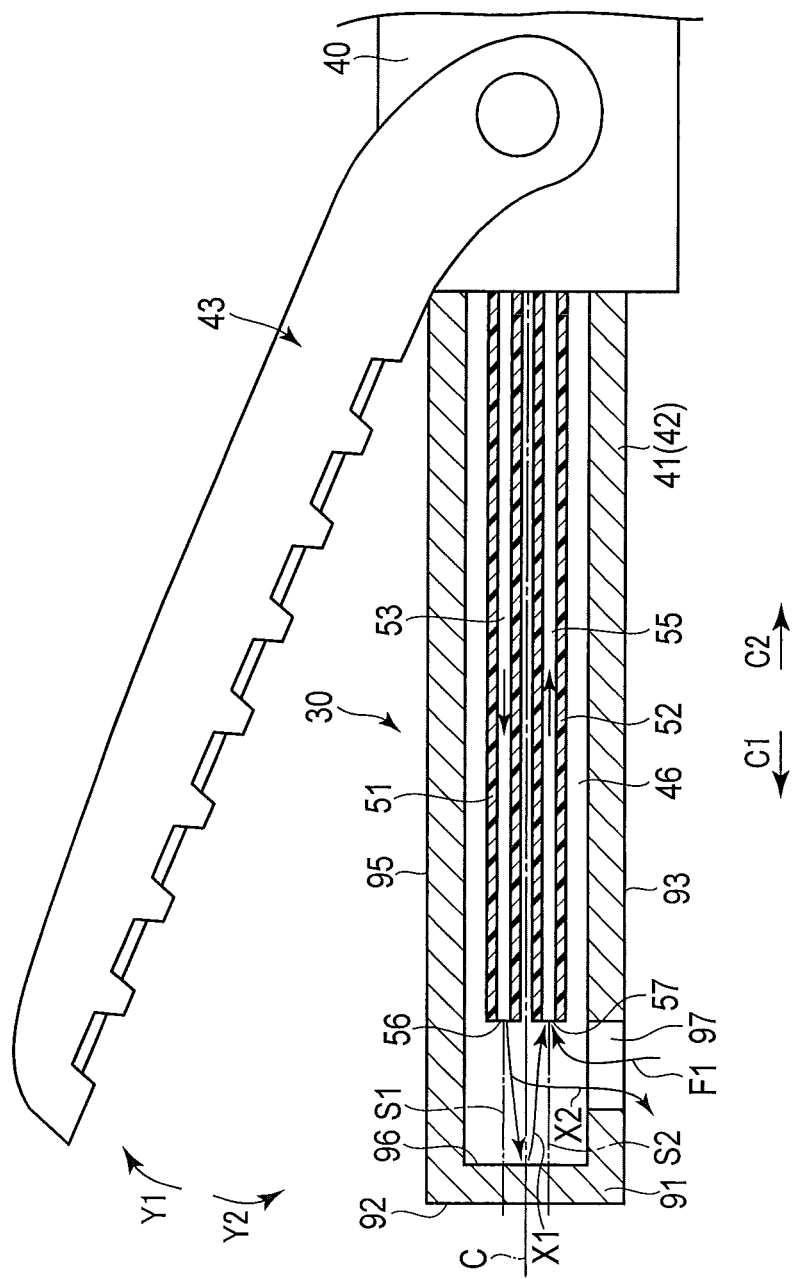
F I G. 15

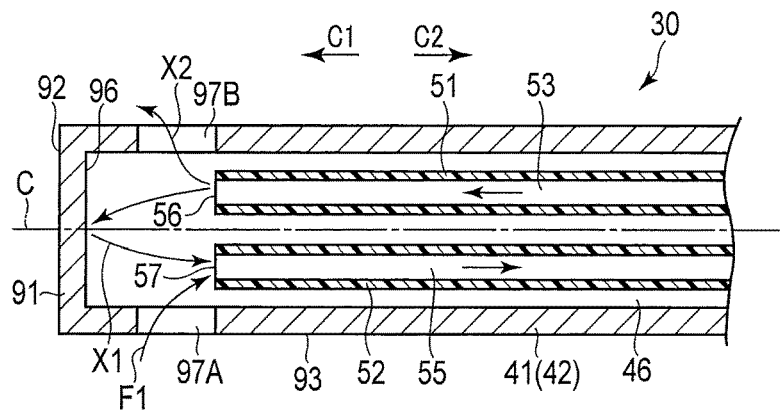
F I G. 16
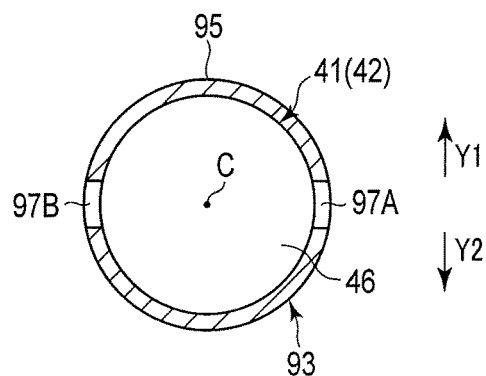
F I G. 17
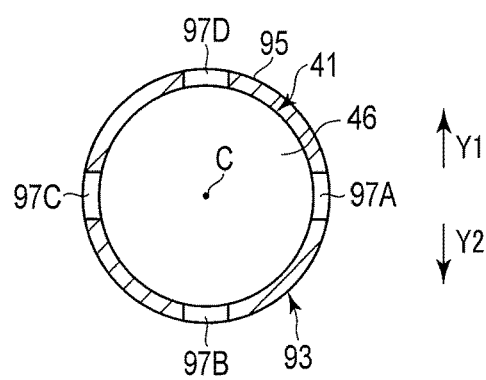
F I G. 18

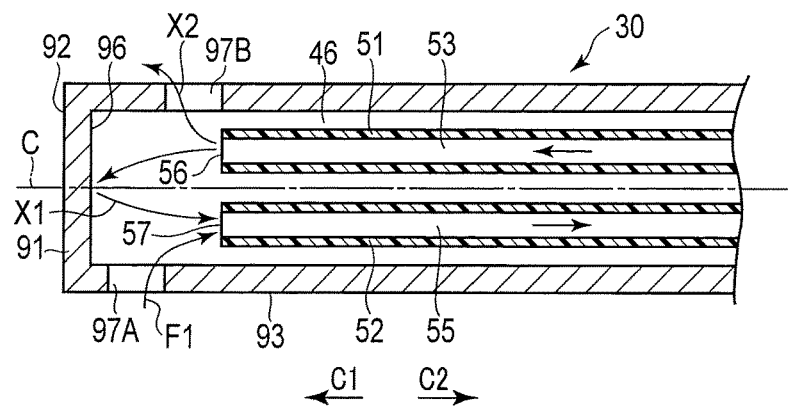
F I G. 19
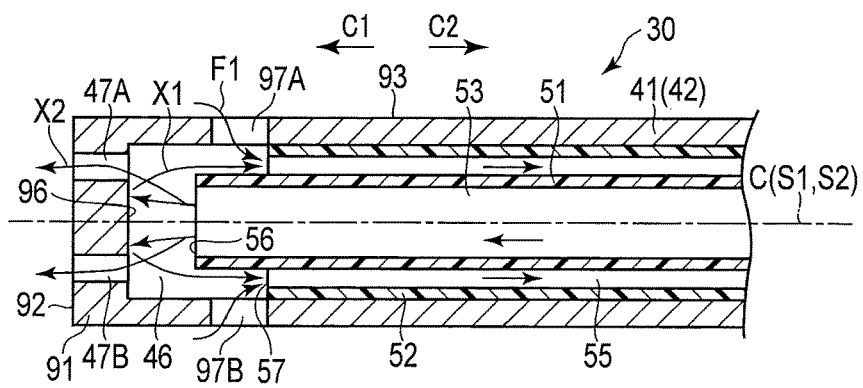
F I G. 20
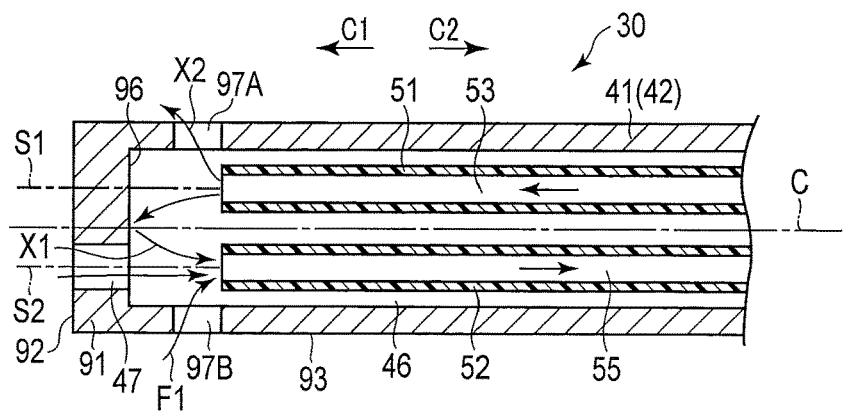
F I G. 21

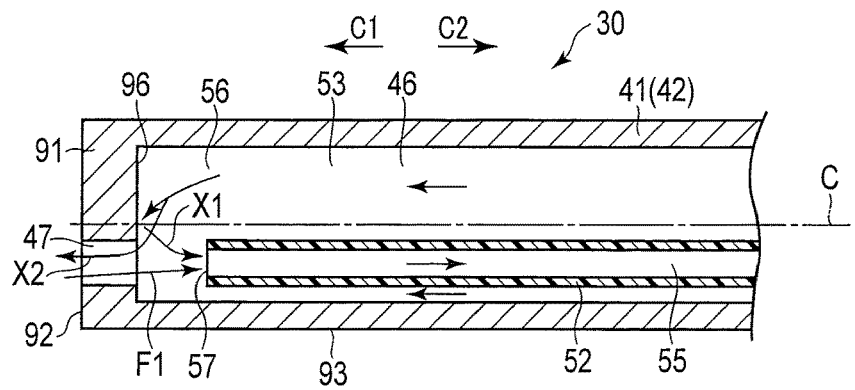
F I G. 22
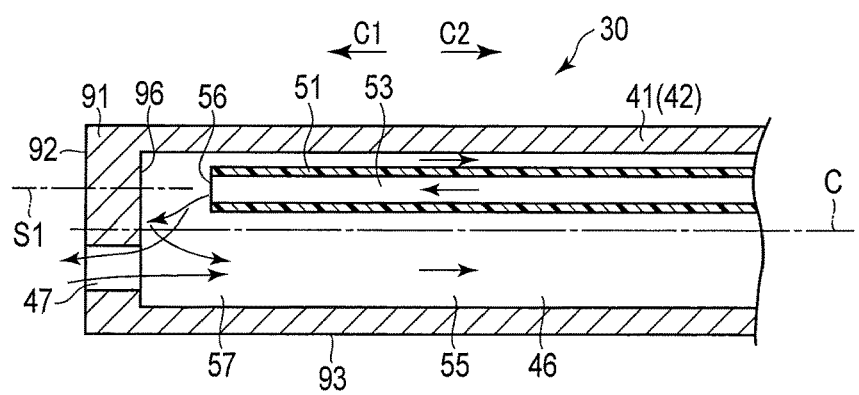
F I G. 23
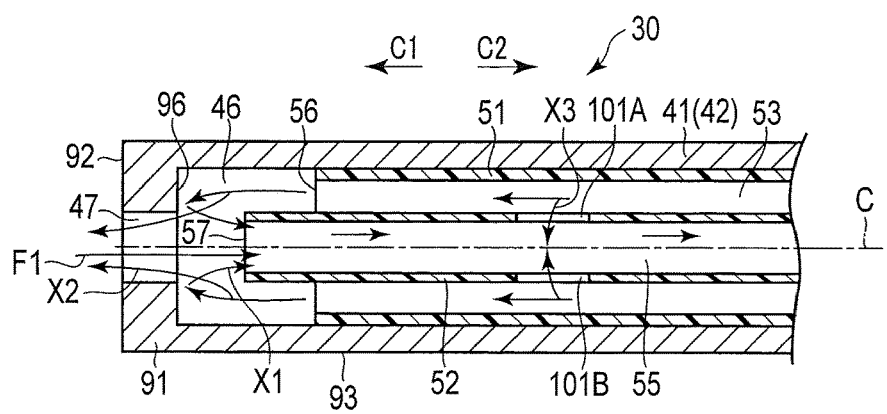
F I G. 24

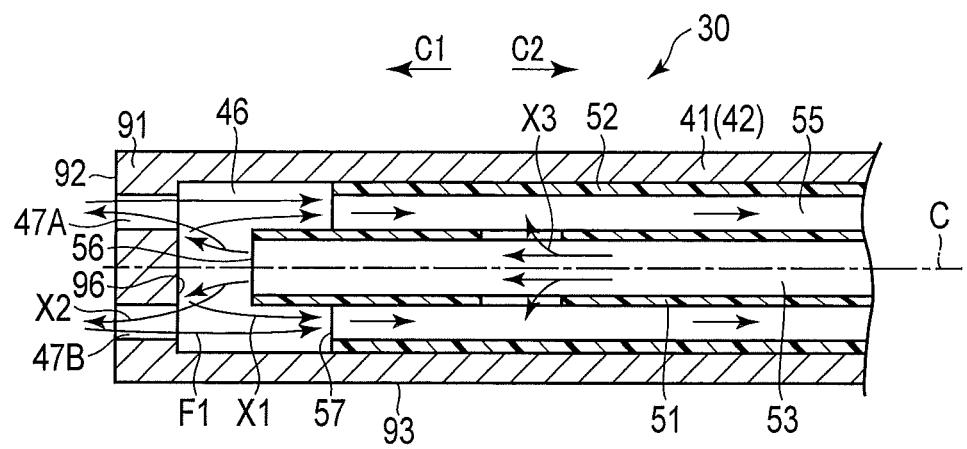
F I G. 25
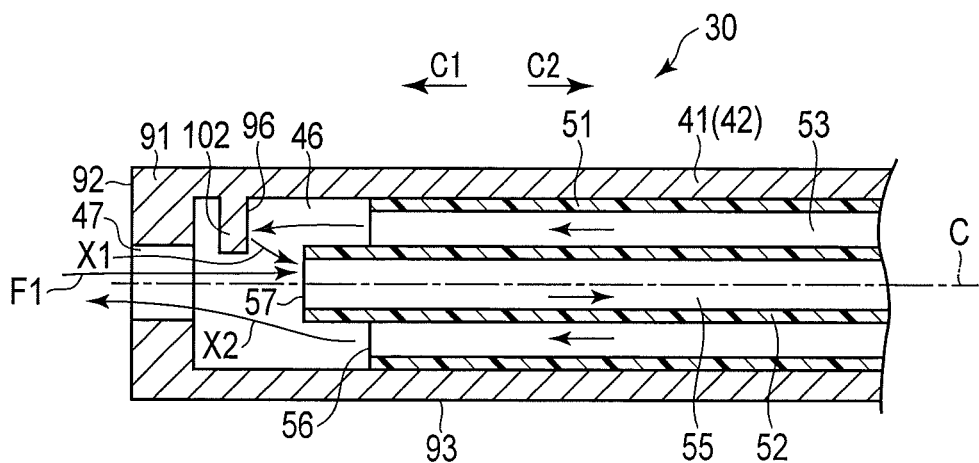
F I G. 26

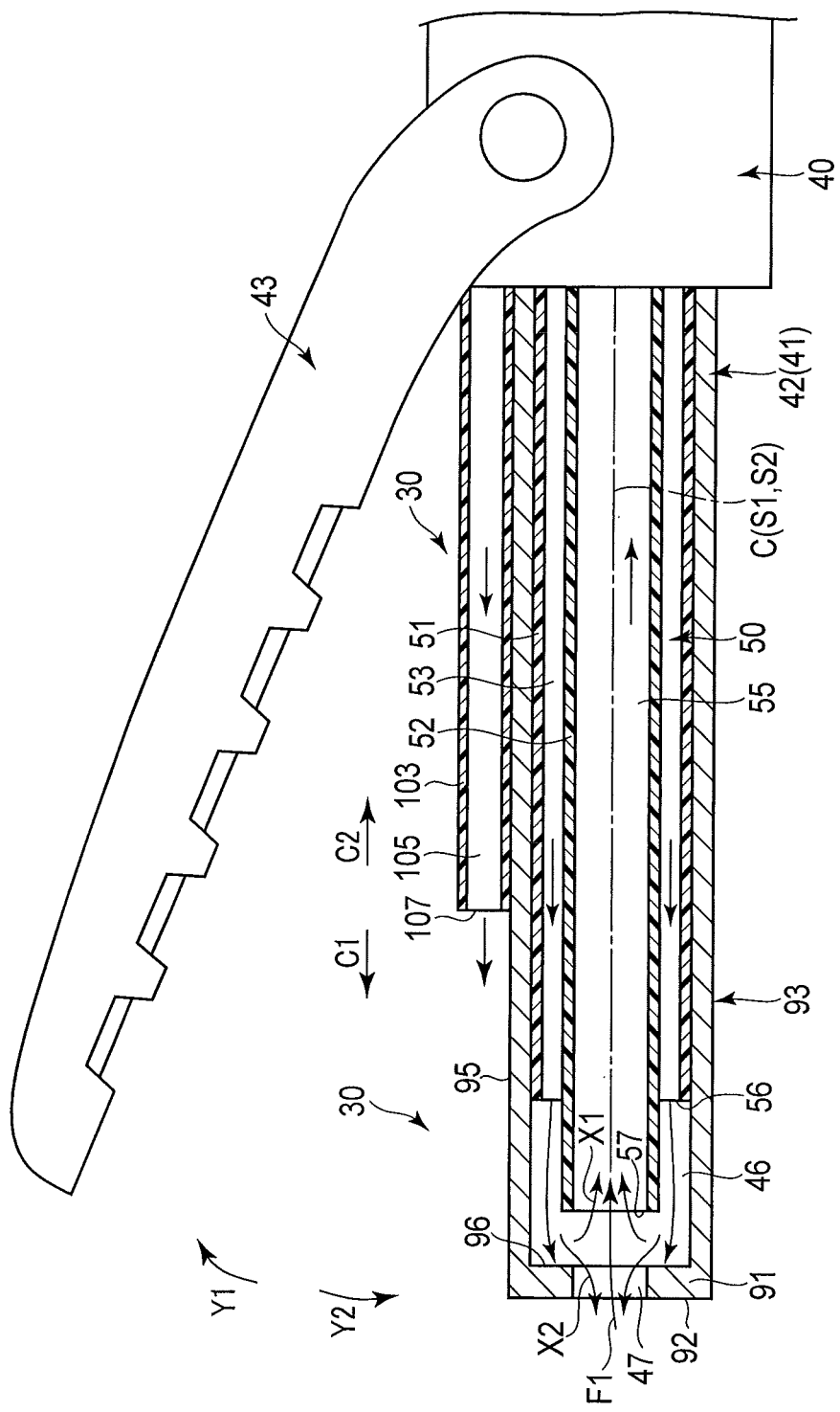
F I G. 27

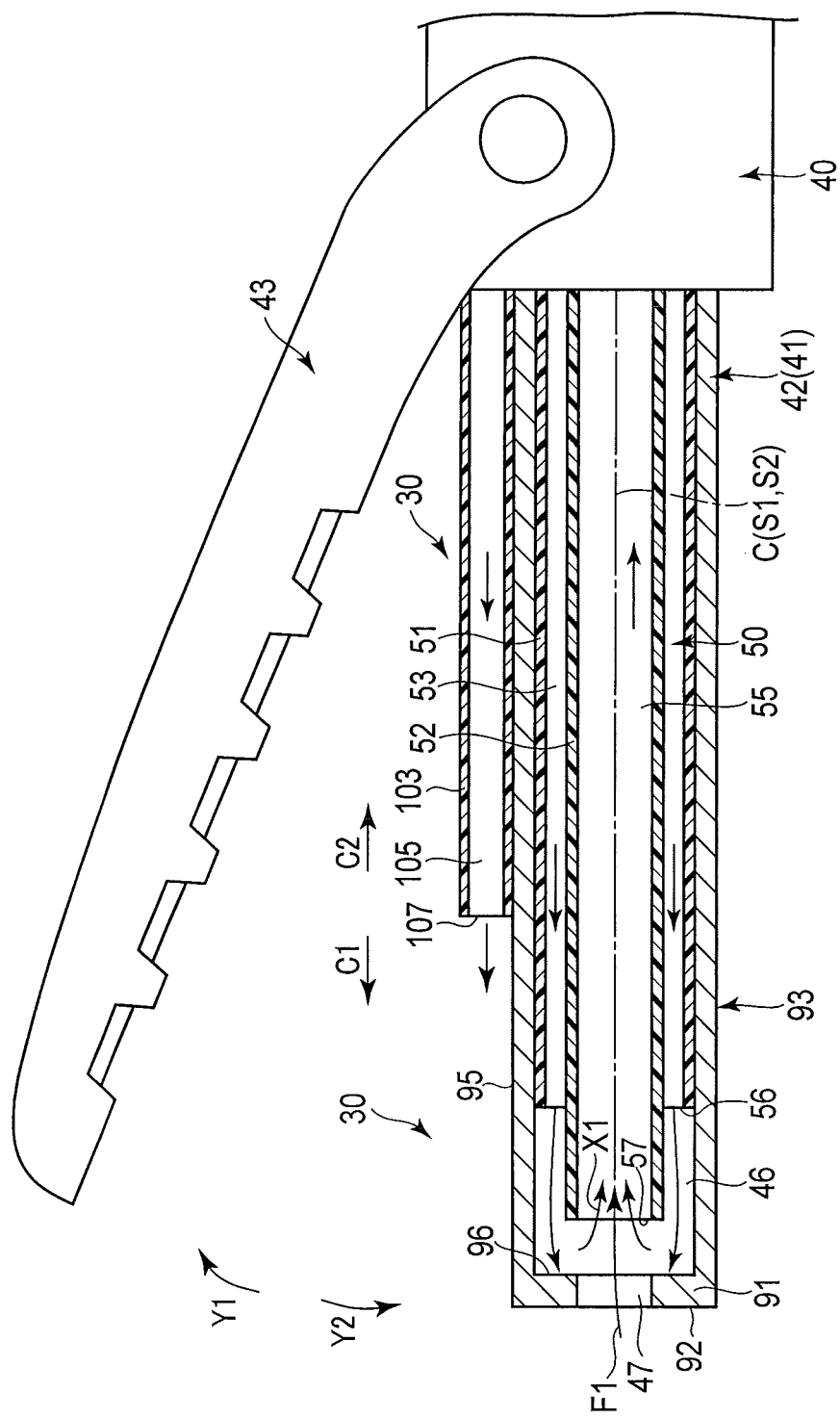
F I G. 28

ENERGY TREATMENT UNIT, ENERGY TREATMENT INSTRUMENT AND ENERGY TREATMENT SYSTEM

CROSS-REFERENCE TO RELATED APPLICATIONS

This is a Continuation Application of PCT Application No. PCT/JP2015/062864, filed Apr. 28, 2015 and based upon and claiming the benefit of priority from prior Japanese Patent Application No. 2014-126626, filed Jun. 19, 2014, the entire contents of which are incorporated herein by reference.

BACKGROUND OF THE INVENTION

1. Field of the Invention

The present invention relates to an energy treatment unit configured such that a treatment section, which performs a treatment by using transmitted energy, is provided in a distal portion of a probe which can transmit energy, and a suction conduit extends in a hollow portion in the inside of the probe. In addition, the invention relates to an energy treatment instrument and an energy treatment system each including the energy treatment unit.

2. Description of the Related Art

U.S. Patent Application Publication No. 2007/0162050 discloses a treatment instrument (energy treatment instrument) including a probe which extends along a longitudinal axis. The probe transmits ultrasonic vibration from a proximal direction to a distal direction as energy that is used for a treatment. A treatment section, which is provided in a distal portion of the probe, treats a treated target such as a biological tissue, by using the transmitted ultrasonic vibration. The probe is inserted through a sheath in the state in which the treatment section projects toward the distal direction. A space portion is formed between the probe and sheath, and a liquid, such as physiological saline, is supplied in the space portion toward the distal direction side. Specifically, the space portion between the probe and sheath serves as a liquid feed conduit through which the liquid is supplied toward the distal direction side. Then, in a state in which the probe is caused to ultrasonically vibrate, the liquid, which has been supplied, is ejected from the distal end of the liquid feed conduit toward the distal direction side, and thereby cavitation occurs near a distal surface of the probe. A biological tissue with low resiliency, such as hepatic cells, is crushed and emulsified. In addition, a hollow portion is formed along the longitudinal axis in the inside of the probe, and the hollow portion is open to the outside of the probe at an opening portion of the distal surface of the probe. The treated target (biological tissue), which was crushed and emulsified by the cavitation, is sucked into the hollow portion through the opening portion, and moves in the hollow portion toward the proximal direction. Specifically, the hollow portion in the inside of the probe serves as a suction conduit through which sucked object moves toward the proximal direction.

BRIEF SUMMARY OF THE INVENTION

According to one aspect of the invention, an energy treatment unit includes that: a probe including a probe distal portion and a probe proximal portion, and extending along a longitudinal axis, a hollow portion being formed in an inside of the probe along the longitudinal axis, and the probe being configured to be capable of transmitting energy from the probe proximal portion toward the probe distal portion; a treatment section provided in the probe distal portion of the probe, and having an outer surface on which an opening portion, through which the hollow portion is open to an outside of the probe, is formed, the treatment section being configured to perform a treatment by using the energy which is transmitted through the probe; a suction conduit extending through the hollow portion from a probe proximal portion direction to a probe distal portion direction, and including a distal end at which a suction port located in the hollow portion is formed, the suction conduit being configured such that suction force occurs from the suction port toward the probe proximal portion direction; a liquid feed conduit extending through the hollow portion from the probe proximal portion direction to the probe distal portion direction, and including a distal end at which an ejection port located in the hollow portion is formed, the liquid feed conduit being configured to eject liquid from the ejection port toward a probe distal portion direction side; and a collision surface provided in the probe in such a state as to be opposed to at least a part of the ejection port, the collision surface being located on the probe distal portion direction side with respect to the suction port and the ejection port, and the collision surface being configured such that at least part of the liquid ejected from the ejection port collides with the collision surface in the hollow portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view illustrating the configuration of an energy treatment system according to a first embodiment;

FIG. 5 is a cross-sectional view which schematically illustrates the configuration of a conduit unit according to the first embodiment;

FIG. 8 is a schematic view illustrating the configuration of a state setting unit 85 according to the first embodiment;

FIG. 9 is a schematic view illustrating a variation with time of longitudinal vibration at a certain position of the treatment section, in a state in which energy is being output in a fourth output mode from an energy source unit according to the first embodiment;

FIG. 15 is a schematic view illustrating, in partial cross section, the configuration of a distal portion of an energy treatment instrument including a treatment section and a jaw according to a fifth modification;

FIG. 16 is a cross-sectional view which schematically illustrates the configuration of a treatment section of a probe and a distal portion of a conduit unit according to a sixth modification;

FIG. 17 is a cross-sectional view which schematically illustrates a cross section passing through an opening portion of the treatment section according to the sixth modification, and being perpendicular to the longitudinal axis;

FIG. 18 is a cross-sectional view which schematically illustrates a cross section passing through an opening portion of a treatment section according to a seventh modification, and being perpendicular to the longitudinal axis;

FIG. 19 is a cross-sectional view which schematically illustrates the configuration of a treatment section of a probe and a distal portion of a conduit unit according to an eighth modification;

FIG. 20 is a cross-sectional view which schematically illustrates the configuration of a treatment section of a probe and a distal portion of a conduit unit according to a ninth modification;

FIG. 21 is a cross-sectional view which schematically illustrates the configuration of a treatment section of a probe and a distal portion of a conduit unit according to a tenth modification;

FIG. 22 is a cross-sectional view which schematically illustrates the configuration of a treatment section of a probe and a distal portion of a conduit unit according to an eleventh modification;

FIG. 23 is a cross-sectional view which schematically illustrates the configuration of a treatment section of a probe and a distal portion of a conduit unit according to a twelfth modification;

FIG. 24 is a cross-sectional view which schematically illustrates the configuration of a treatment section of a probe and a distal portion of a conduit unit according to a 13th modification;

FIG. 25 is a cross-sectional view which schematically illustrates the configuration of a treatment section of a probe and a distal portion of a conduit unit according to a 14th modification;

FIG. 26 is a cross-sectional view which schematically illustrates the configuration of a treatment section of a probe and a distal portion of a conduit unit according to a 15th modification;

FIG. 27 is a schematic view illustrating, in partial cross section, the configuration of a distal portion of an energy treatment instrument including a treatment section and a jaw according to a 16th modification;

FIG. 28 is a schematic view illustrating, in partial cross section, the configuration of a distal portion of an energy treatment instrument including a treatment section and a jaw according to a 17th modification;

DETAILED DESCRIPTION OF THE INVENTION

First Embodiment

Figure 2:
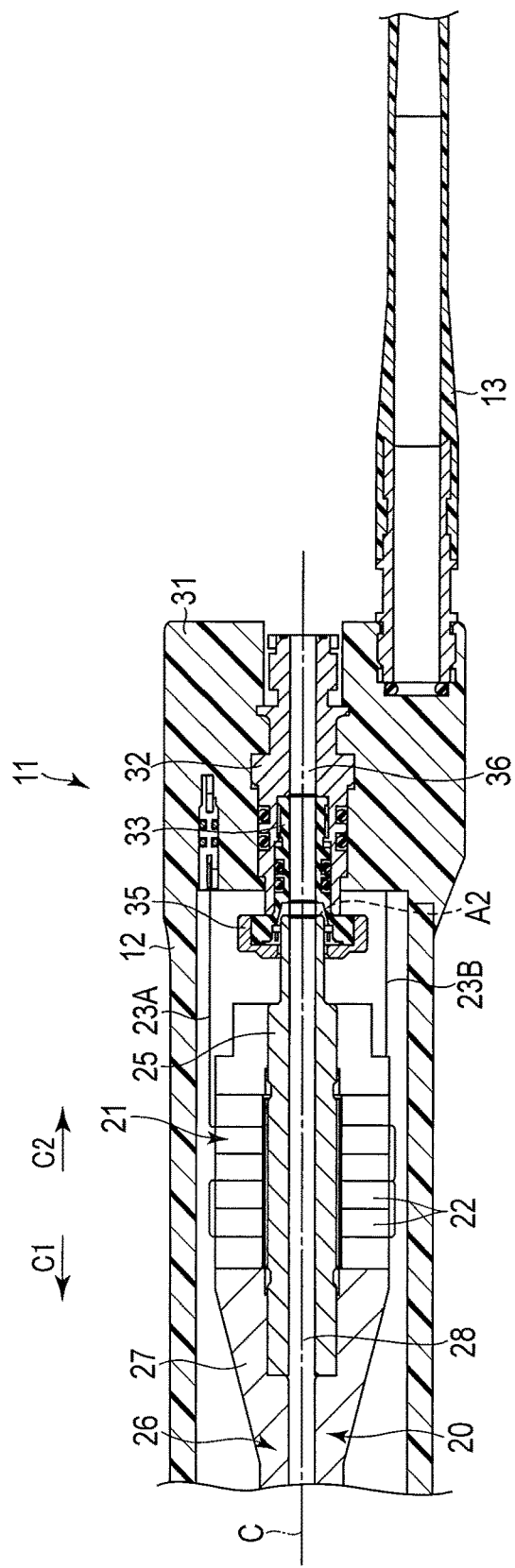
FIG. 2 is a cross-sectional view which schematically illustrates the configuration of a transducer unit according to the first embodiment.

A first embodiment of the present invention will be described with reference to FIG. 1 to FIG. 9.

FIG. 1 is a view illustrating the configuration of an energy treatment system 1 of the present embodiment. As illustrated in FIG. 1, the energy treatment system 1 includes an energy treatment instrument (handpiece) 2. The energy treatment instrument 2 has a longitudinal axis C. Here, a direction parallel to the longitudinal axis C is set as a longitudinal direction. One side in the longitudinal direction is a distal direction (a direction of arrow C1 in FIG. 1), and the side opposite to the distal direction is a proximal direction (a direction of arrow C2 in FIG. 1). In this embodiment, the energy treatment instrument 2 is an ultrasonic treatment instrument which treats a treated target, such as a biological tissue, by using ultrasonic vibration as energy, and is also a high-frequency treatment instrument which treats the treated target by using high-frequency electric power (high-frequency current) as energy.

The energy treatment instrument 2 includes a holding unit (handle unit) 3. The holding unit 3 includes a cylindrical case portion 5 which extends along the longitudinal axis C, and a stationary handle 6 which extends from the cylindrical case portion 5 in a certain direction crossing the longitudinal axis C. The cylindrical case portion 5 and stationary handle 6 are formed as one piece. A movable handle 7 is rotatably attached to the cylindrical case portion 5. By the movable handle 7 rotating about the position of attachment to the cylindrical case portion 5, the movable handle 7 opens or closes relative to the stationary handle 6. In the present embodiment, the movable handle 7 is located on the distal direction side with respect to the stationary handle 6. In addition, the holding unit 3 includes a rotary operation knob 8 which is a rotary operation input section that is attached to a distal direction side of the cylindrical case portion 5. The rotary operation knob 8 is rotatable about the longitudinal axis C relative to the cylindrical case portion 5.

In addition, energy operation input buttons 9A to 9C, which are energy operation input sections, are attached to the cylindrical case portion 5 of the holding unit 3. The energy operation input buttons 9A and 9B are located on the side where the stationary handle 6 is located, with reference to the longitudinal axis C as the center. Besides, in this embodiment, the energy operation input buttons 9A and 9B are located on the distal direction side with respect to the stationary handle 6. The energy operation input button 9C is located on the side opposite to the side where the stationary handle 6 is located, with reference to the longitudinal axis C as the center. The energy operation input buttons 9A to 9C are detachably attached to the cylindrical case portion 5.

The energy treatment instrument 2 includes a transducer unit 11. The transducer unit 11 includes a transducer case 12. The transducer case 12 is rotatable about the longitudinal axis C relative to the cylindrical case portion 5 with the rotary operation knob 8. The transducer case 12 is attached to the holding unit 3, by the transducer case 12 being inserted into the inside of the cylindrical case portion 5 from the proximal direction side. One end of a cable 13 is connected to the oscillator case 12. The energy treatment system 1 includes an energy source unit 15 which is, for example, an energy control device. The other end of the cable 13 is connected to the energy source unit 15. In the present embodiment, the energy source unit 15 includes an ultrasonic energy source 16, a high-frequency energy source 17, and a controller 18. Each of the ultrasonic energy source 16 and high-frequency energy source 17 is composed of, for example, power supply and converter circuit. The controller 18 is composed of a processor which includes, for example, a CPU (Central Processing Unit) or an ASIC (Application Specific Integrated Circuit). In addition, the energy source unit 15 is electrically connected to an energy operation input switch 10 such as a footswitch, which is an energy operation input section. The energy operation input switch 10 is provided as a separated body from the energy treatment instrument 2.

FIG. 2 is a view illustrating the configuration of the transducer unit 11. As illustrated in FIG. 2, the transducer unit 11 includes an ultrasonic transducer 21 which is a vibration causing section that is provided in the inside of the transducer case 12. The ultrasonic transducer 21 includes a plurality (six in this embodiment) of piezoelectric elements 22 which convert an electric current (AC current) to ultrasonic vibration. One end of each of electric path portions 23A and 23B is connected to the ultrasonic oscillator 21. The electric path portions 23A and 23B extend through the inside of the cable 13, and the other ends of the electric path portions 23A and 23B are connected to the ultrasonic energy source 16 of the energy source unit 15. The electric path portions 23A and 23B are formed of electric wiring lines which extend in the inside of the transducer case 12, and electric wiring lines which extend in the inside of the cable 13. Ultrasonic electric power (ultrasonic energy) is supplied from the ultrasonic energy source 16 to the ultrasonic transducer 21 via the electric path portions 23A and 23B, and thereby ultrasonic vibration is caused by the ultrasonic transducer 21. Specifically, the ultrasonic energy source 16 outputs ultrasonic electric power which is energy that is supplied to the ultrasonic transducer 21. Then, by the supply of the ultrasonic electric power (AC current), ultrasonic vibration is caused by the ultrasonic transducer 21 as energy that is used for a treatment.

The ultrasonic transducer 21 is attached to a cylindrical elements-attached member 25. The ultrasonic transducer 21, which includes the piezoelectric elements 22, is fixed to an outer peripheral surface of the elements-attached member 25. A cylindrical horn member 26 is connected to a distal direction side of the elements-attached member 25. The horn member 26 is continuous with a distal direction side of the ultrasonic transducer 21. The horn member 26 includes a cross-sectional area varying portion 27 having a cross-sectional area perpendicular to the longitudinal axis C, which gradually decreases toward the distal direction. The ultrasonic vibration, which is caused by the ultrasonic transducer 21, is transmitted to the horn member 26, and is transmitted in the horn member 26 from the proximal direction to the distal direction. The amplitude of the ultrasonic vibration, which is transmitted to the horn member 26, is increased in the cross-sectional area varying portion 27. In addition, since the horn member 26 and elements-attached member 25 are formed in cylindrical shapes, a cavity portion 28 is formed in the inside of the horn member 26 and in the inside of the elements-attached member 25. The cavity portion 28 extends along the longitudinal axis C from a proximal end of the elements-attached member 25 to a distal end of the horn member 26.

As illustrated in FIG. 2, the transducer case 12 is provided with a case proximal wall 31 which forms a proximal end of the transducer case 12, and a cylindrical connection member 32 is fixed to the case proximal wall 31. The connection member 32 projects from the case proximal wall 31 toward the distal direction in the inside of the transducer case 12. The connection member 32 is coupled to the elements-attached member 25 from the proximal direction side via a cylindrical vibration damping member 33. In addition, the vibration damping member 33 is clamped between the connection member 32 and a removal prevention member 35 in the longitudinal direction that is parallel to the longitudinal axis C, and the movement of the vibration damping member 33 in the longitudinal direction relative to the connection member 32 and elements-attached member 25 is restricted.

Since the connection member 32 and vibration damping member 33 are formed in cylindrical shapes, a space portion 36 is formed in the inside of the connection member 32 and in the inside of the vibration damping member 33. The space portion 36 extends along the longitudinal axis C from a proximal end of the connection member 32 to a distal end of the vibration damping member 33. A distal end of the space portion 36 communicates with a proximal end of the cavity portion 28 which extends in the inside of the elements-attached member 25. In addition, a proximal end of the space portion 36 is open to the outside of the transducer unit 11 (the outside of the transducer case 12).

As illustrated in FIG. 1, the energy treatment instrument 2 includes a sheath 40 which extends along the longitudinal axis C. The sheath 40 is attached to the holding unit 3, by the sheath 40 being inserted into the inside of the rotary operation knob 8 and the inside of the cylindrical case portion 5 from the distal direction side. Specifically, the holding unit 3 is coupled to a proximal direction side of the sheath 40. In the inside of the cylindrical case portion 5, the sheath 40 is attached to a distal direction side of the transducer case 12. In addition, the energy treatment instrument 2 includes a probe (ultrasonic probe) 41 which is inserted through the sheath 40. The probe 41 extends along the longitudinal axis C toward the distal direction from the inside of the holding unit 3 (the inside of the cylindrical case portion 5) through the inside of the sheath 40. In this embodiment, the longitudinal axis C agrees with the center axis of the probe 41. The probe 41 includes a probe distal portion and a probe proximal portion, and extends along the longitudinal axis C from the probe proximal portion toward the probe distal portion. The probe distal portion of the probe 41 is provided with a treatment section 42. Here, a direction toward the probe distal portion in the probe 41 is defined as a probe distal portion direction, and a direction toward the probe proximal portion in the probe 41 is defined as a probe proximal portion direction. In the present embodiment, the probe distal portion direction agrees with the above-described distal direction, and the probe proximal portion direction agrees with the above-described proximal direction. The treatment section 42 projects from a distal end of the sheath 40 toward the probe distal portion direction.

In addition, a jaw 43 is rotatably attached to a distal portion of the sheath 40. By opening or closing the movable handle 7 relative to the stationary handle 6, a movable portion (not shown) provided in the sheath 40 moves along the longitudinal axis C. Thereby, the jaw 43 rotates, and the jaw 43 opens or closes relative to the treatment section 42 of the probe 41. The sheath 40, probe 41 and jaw 43 can rotate with the rotary operation knob 8 about the longitudinal axis C relative to the cylindrical case portion 5.

Figure 3:
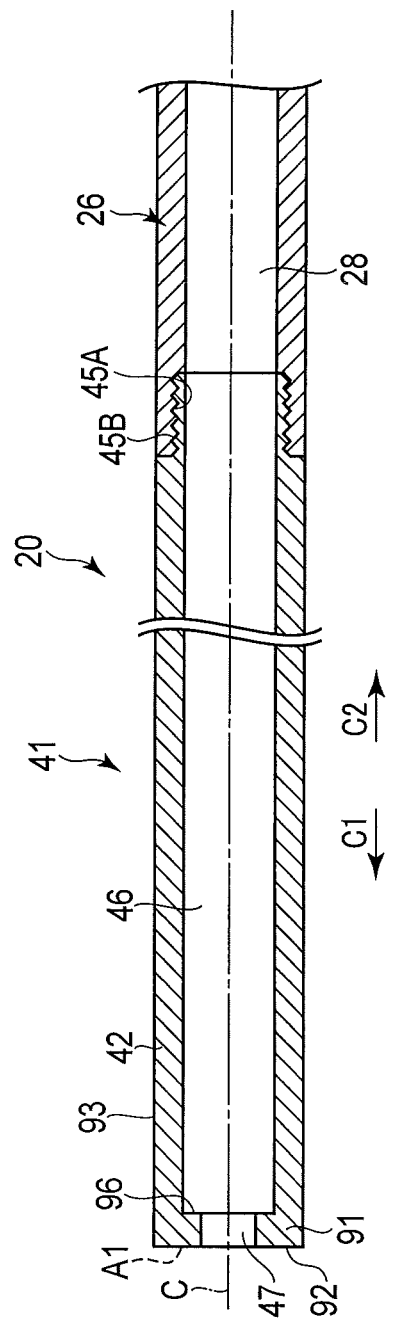
FIG. 3 is a cross-sectional view which schematically illustrates the configuration of a probe and a distal portion of a horn member according to the first embodiment.

FIG. 3 is a view illustrating the configuration of the probe 41 and a distal portion of the horn member 26. As illustrated in FIG. 3, the probe 41 extends along the longitudinal axis C. A female screw portion 45A is formed in the distal portion of the horn member 26, and a male screw portion 45B is formed in a proximal portion of the probe 41. By the male screw portion 45B being engaged with the female screw portion 45A, the probe 41 is connected to the distal direction side of the horn member 26. The probe 41 is connected to the horn member 26 in the inside of the cylindrical case portion 5 of the holding unit 3.

A hollow portion 46 is formed along the longitudinal axis C in the inside of the probe 41. The hollow portion 46 extends from the probe proximal portion of the probe 41 to the probe distal portion (treatment section 42) of the probe 41. The hollow portion 46 is open to the outside of the probe 41 at an opening portion 47 which is located on an outer surface of the treatment section 42. The opening portion 47 establishes communication between the hollow portion 46 in the inside of the probe 41 and the outside of the probe 41. In the state in which the probe 41 is connected to the horn member 26, a proximal end of the hollow portion 46 communicates with a distal end of the cavity portion 28 which extends in the inside of the horn member 26. Accordingly, in the state in which the probe 41 is connected to the horn member 26, the opening portion 47 of the hollow portion 46 communicates with the proximal end of the space portion 36 via the hollow portion 46, cavity portion 28 and space portion 36.

Vibration, which has been transmitted from the ultrasonic transducer 21 to the horn member 26, is transmitted to the ultrasonic probe 41. Further, the probe 41, which is the ultrasonic probe, transmits ultrasonic vibration, which is energy, from the probe proximal portion direction to the probe distal portion direction. In addition, the treatment section 42 performs treatment by using the transmitted ultrasonic vibration. At this time, a vibrating body unit 20, which transmits ultrasonic vibration caused by the ultrasonic transducer 21 and vibrates by the ultrasonic vibration, is constituted by the elements-attached member 25, horn member 26 and probe 41. In the meantime, the amplitude of vibration by ultrasonic vibration does not large in the elements-attached member 25 which is located on the proximal side with respect to the cross-sectional area varying portion 27 of the horn member 26. In addition, the ultrasonic vibration, which is transmitted from the elements-attached member 25 to the probe proximal portion direction, is damped by the vibration damping member 33. Thus, the ultrasonic vibration is not transmitted from the elements-attached member 25 (vibrating body unit 20) to the connection member 32 and transducer case 12, and the connection member 32 and transducer case 12 do not vibrate by the ultrasonic vibration.

The vibrating body unit 20 vibrates in a preset vibration mode (vibration state) which is used at a time of treatment, by transmitting the ultrasonic vibration caused by the ultrasonic transducer 21. In the preset vibration mode, the vibrating body unit 20 performs longitudinal vibration, the vibration direction of which is parallel to the longitudinal axis C (longitudinal direction). In addition, in the preset vibration mode, a distal end of the vibrating body unit 20 (a distal end of the probe 41) and a proximal end of the vibrating body unit 20 (the proximal end of the elements-attached member 25) are at antinode positions of the longitudinal vibration. Here, an antinode position A1, which is located at the distal end of the vibrating body unit 20, is located most on the probe distal portion direction side among the antinode positions of longitudinal vibration, and an antinode position A2, which is located at the proximal end of the vibrating body unit 20, is located most on the probe proximal portion direction side among the antinode positions of longitudinal vibration. In addition, in the established vibration mode, the number of antinode positions of longitudinal vibration and the number of node positions of longitudinal vibration between the distal end of the vibrating body unit 20 and the proximal end of the vibrating body unit 20 are fixed, and at least one node position of longitudinal vibration exists between the distal end of the vibrating body unit 20 and the proximal end of the vibrating body unit 20. The controller 18 adjusts the frequency of an electric current (AC current) which is supplied from the ultrasonic energy source 16 to the ultrasonic transducer 21, thereby adjusting the resonance frequency of the vibrating body unit 20 and causing the vibrating body unit 20 to vibrate in the preset vibration mode. In the meantime, the preset vibration mode (i.e. the number of node positions and antinode positions of longitudinal vibration) is determined in accordance with the dimension in the longitudinal direction of the used vibrating body unit 20, the kind of treatment, etc.

In addition, the elements-attached member 25 is electrically connected to the high-frequency energy source 17 of the energy source unit 15 via an electric path portion (not shown). The electric path portion is formed of an electric wiring line which extends in the inside of the transducer case 12, and an electric wiring line which extends in the inside of the cable 13. The high-frequency energy source 17 outputs high-frequency electric power (high-frequency energy) as energy that is used for a treatment. The high-frequency electric power, which is output from the high-frequency energy source 17, is supplied to the treatment section 42 through the electric path portion (not shown), elements-attached member 25, horn member 26 and probe 41. Specifically, a probe-side electricity supply path P1 of high-frequency electric power, which is output from the high-frequency energy source 17, is formed by the electric path portion (not shown), elements-attached member 25, horn member 26 and probe 41. The treatment section 42 functions as an electrode, by the high-frequency electric power being supplied (transmitted) to the treatment section 42 via the probe-side electricity supply path P1.

In addition, the transducer case 12 is provided with an electric conductor portion (not shown). The electric conductor portion of the transducer case 12 is electrically connected to an electric conductor portion (not shown) of the jaw 43 via an electric conductor portion (not shown) of the sheath 40. Besides, the electric conductor portion of the transducer case 12 is electrically connected to the high-frequency energy source 17 of the energy source unit 15 via an electric path portion (not shown). The electric path portion is formed of a part that is different from a part which forms the probe-side electricity supply path P1, and is formed of an electric wiring line which extends in the inside of the transducer case 12, and an electric wiring line which extends in the inside of the cable 13. The high-frequency electric power, which is output from the high-frequency energy source 17, is supplied to the electric conductor portion of the jaw 43 through the electric path portion (not shown), the electric conductor portion of the transducer case 12 and the electric conductor portion of the sheath 40. Specifically, a jaw-side electricity supply path P2 of high-frequency electric power, which is output from the high-frequency energy source 17, is formed by the electric path portion (not shown), the electric conductor portion of the transducer case 12 and the electric conductor portion of the sheath 40. The electric conductor portion of the jaw 3 functions as an electrode which is different in electric potential from the treatment section 42, by the high-frequency electric power being supplied (transmitted) to the electric conductor portion of the jaw 3 via the jaw-side electricity supply path P2.

In the meantime, the probe 41 is supported by the sheath 40 via a support member (not shown) which is formed of an electrically insulating material, and the horn member 26 is supported by the transducer case 12 via a support member (not shown) which is formed of an electrically insulating material. Thus, the probe 41 is prevented from coming in contact with the sheath 40, and the horn member 26 is prevented from coming in contact with the oscillator case 12. Accordingly, short-circuit between the probe-side electricity supply path P1 and jaw-side electricity supply path P2 is prevented. In addition, in the state in which the transducer unit 20 vibrates in the preset vibration mode, each of the above-described support members is located at a node position of longitudinal vibration, and the support member is formed of a material which has a low vibration transmissibility and damps vibration. Thus, no ultrasonic vibration is transmitted from the probe 41 and horn member 26 (vibrating body unit 20) to the sheath 40 and transducer case 12, and the sheath 40 and transducer case 12 do not vibrate due to ultrasonic vibration.

Figure 4:
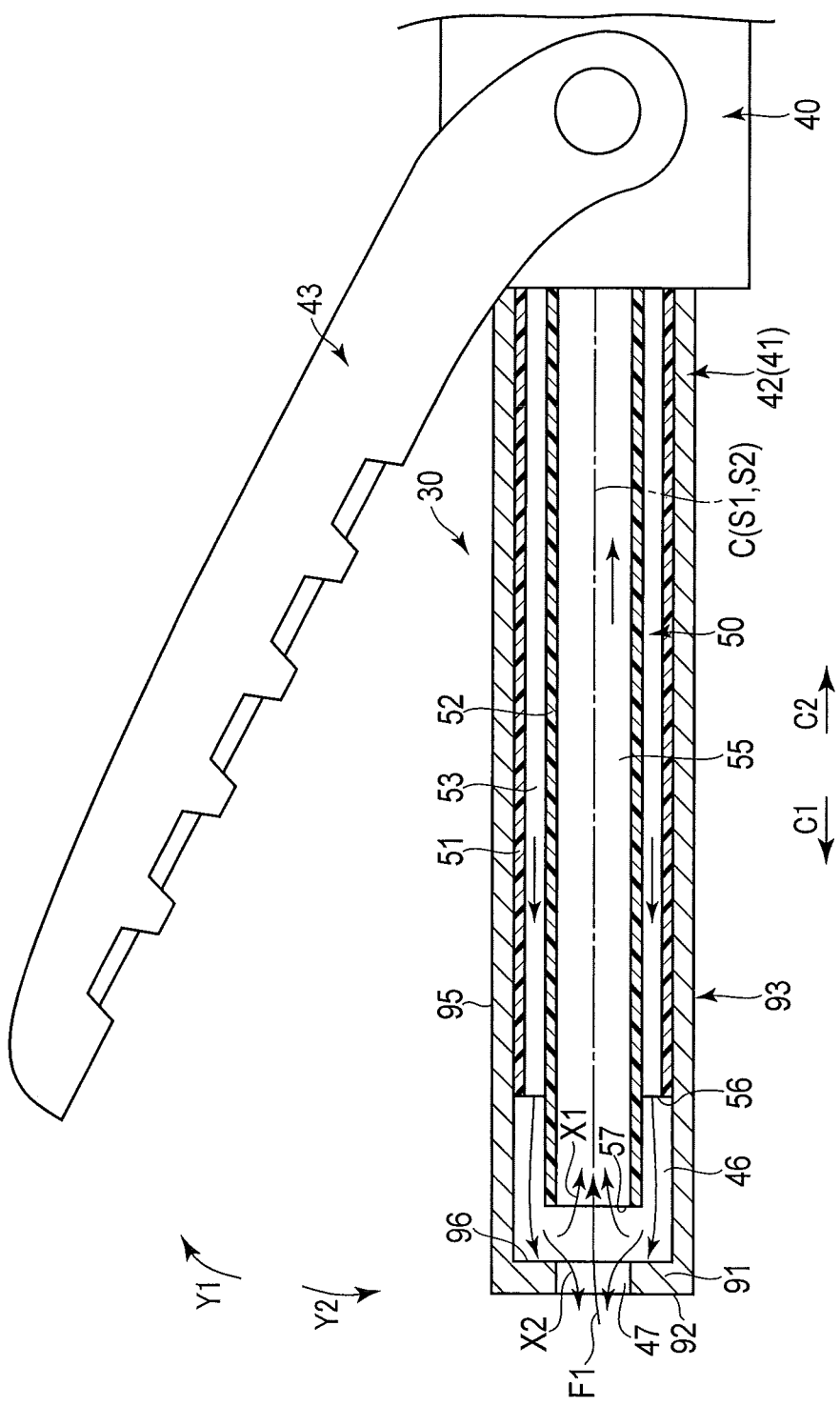
FIG. 4 is a schematic view illustrating, in partial cross section, the configuration of a distal portion of an energy treatment instrument including a treatment section and a jaw according to the first embodiment.

FIG. 4 is a view illustrating the configuration of the distal portion of the energy treatment instrument 2 including the treatment section 42 and jaw 43. As illustrated in FIG. 4, a liquid feed tube 51 and a suction tube 52 extend from the probe proximal portion direction to the probe distal portion direction in the hollow portion 46 in the inside of the probe 41. A conduit unit 50 including the liquid feed tube 51 and suction tube 52 is detachably coupled to the probe 41, holding unit 3 and transducer unit 11. In addition, an energy treatment unit 30, which performs treatment by the treatment section 42 with use of energy, is composed of the probe 41 and conduit unit 50.

FIG. 5 is a view illustrating the configuration of the conduit unit 50. As illustrated in FIG. 4 and FIG. 5, in the conduit unit 50 of this embodiment, the suction tube 52 is inserted through the inside of the liquid feed tube 51. In the inside of the suction tube 52, a suction conduit 55 extends from the probe proximal portion direction to the probe distal portion direction. In the present embodiment, a conduit axis (suction conduit axis) S2, which is the center axis of the suction conduit 55, is coaxial with the longitudinal axis C. In addition, in the conduit unit 50, a liquid feed conduit 53 extends from the probe proximal portion direction to the probe distal portion direction between the inner peripheral surface of the liquid feed tube 51 and the outer peripheral surface of the suction tube 52. In this embodiment, a conduit axis (liquid feed conduit axis) S1, which is the center axis of the liquid feed conduit 53, is coaxial with the longitudinal axis C. As described above, by the conduit unit 50 being coupled to the holding unit 3 and transducer unit 11, the liquid feed conduit 53 and suction conduit 55 extend from the probe proximal portion direction to the probe distal portion direction in the hollow portion 46 of the probe 41. In addition, in this embodiment, the cross section of the suction conduit 55, which is perpendicular to the longitudinal axis C, has a circular shape about the longitudinal axis C (conduit axis S2), and the cross section of the liquid feed conduit 53, which is perpendicular to the longitudinal axis C, has a cylindrical (circular cylindrical) shape surrounding the outer peripheral side of the suction conduit 55.

An ejection port 56 is formed at a distal end of the liquid feed conduit 53. In addition, a suction port 57 is formed at a distal end of the suction conduit 55. The ejection port 56 and suction port 57 are located in a distal portion of the hollow portion 46 which is formed in the inside of the probe 41. Specifically, the liquid feed conduit 53 and suction conduit 55 extend up to the inside of the treatment section 42 toward the probe distal portion direction. In this embodiment, the suction port 57 of the suction conduit 55 is located on the probe distal portion direction side with respect to the ejection port 56 of the liquid feed conduit 53.

Figure 6:
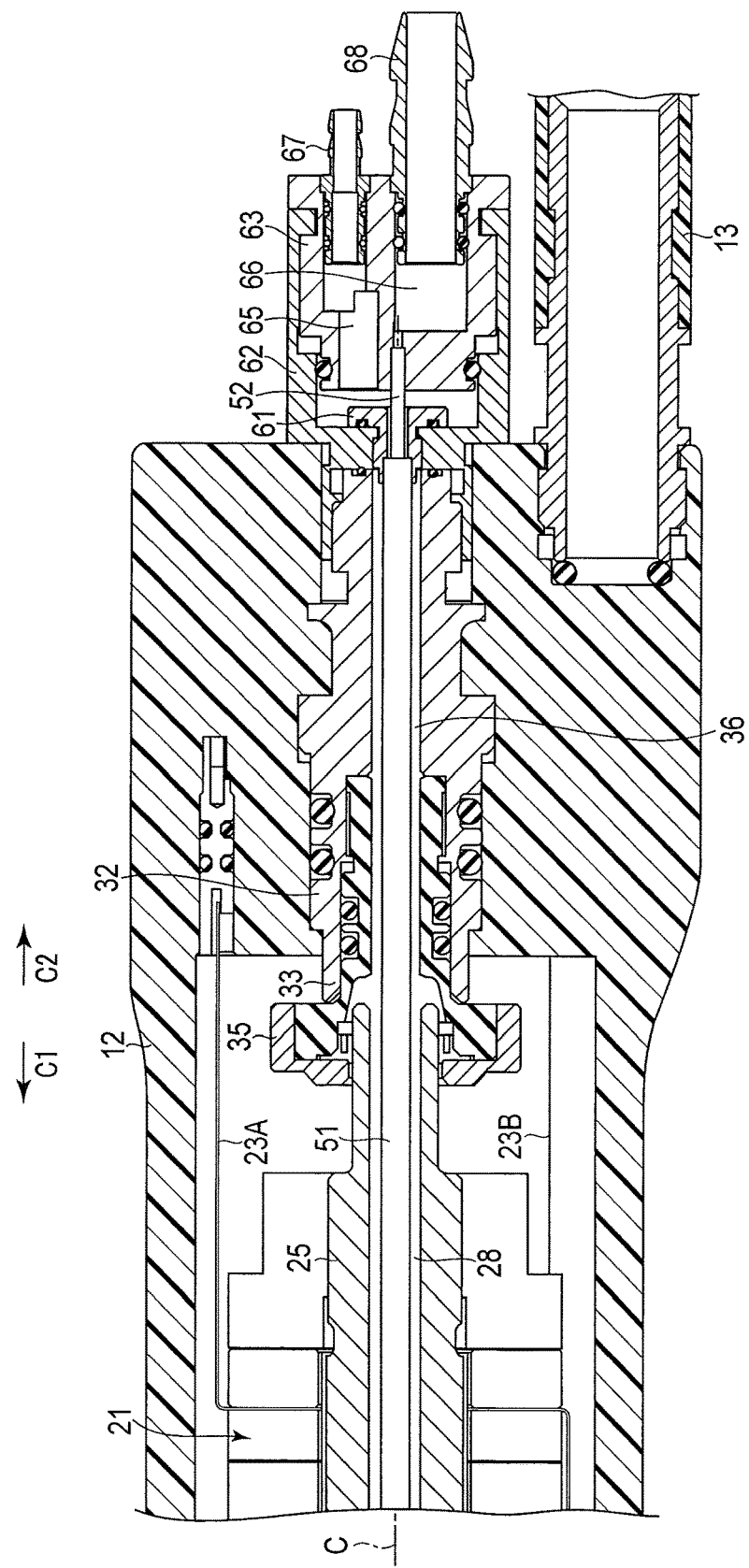
FIG. 6 is a cross-sectional view which schematically illustrates the configuration of a proximal portion of the conduit unit and the transducer unit according to the first embodiment, in a state in which the conduit unit is coupled to the probe, a holding unit and the transducer unit.
Figure 7:
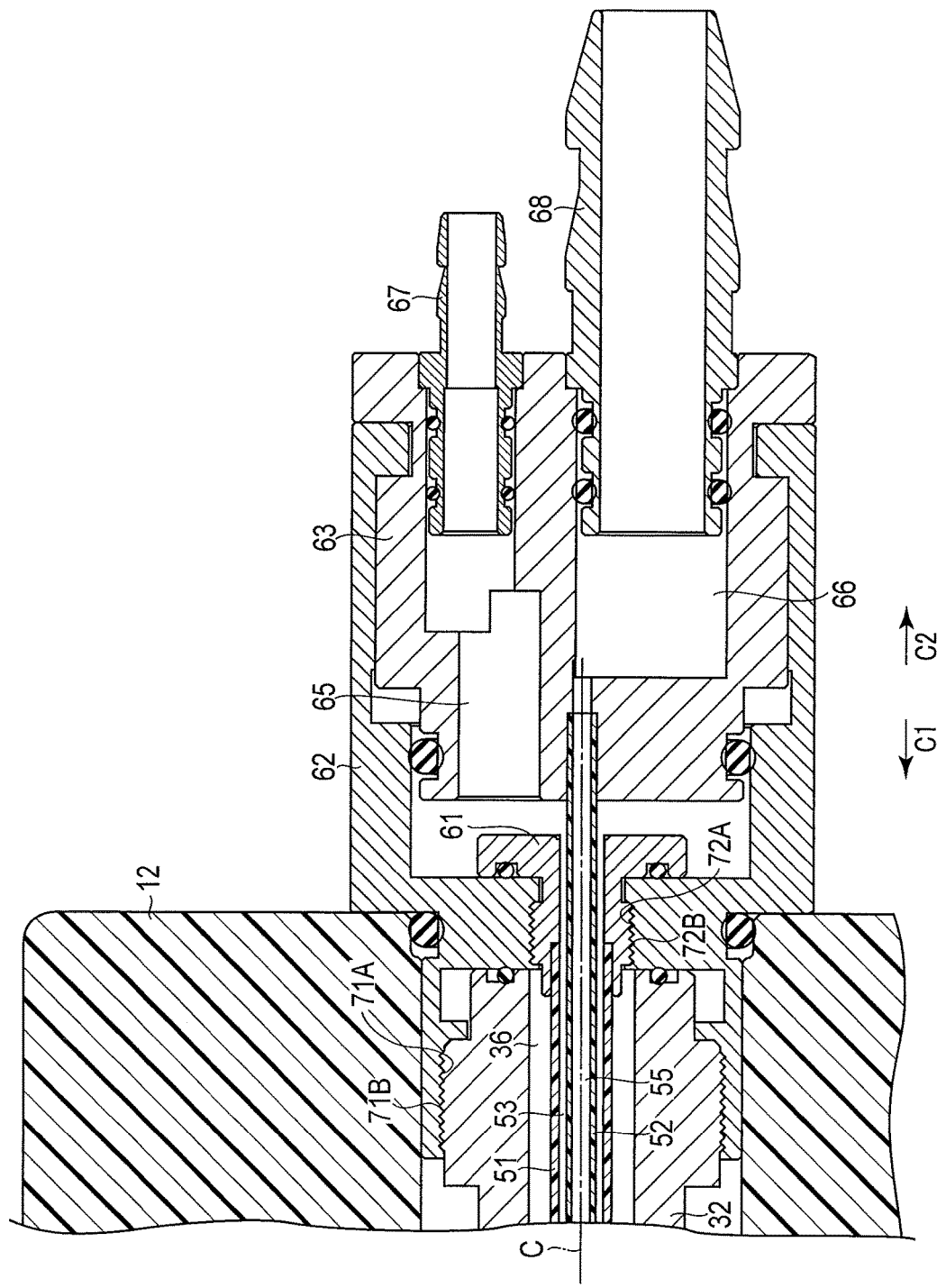
FIG. 7 is a cross-sectional view which schematically illustrates a configuration in which the conduit unit according to the first embodiment is detachably coupled to the probe, holding unit and transducer unit.

FIG. 6 is a view illustrating the configuration of a proximal portion of the conduit unit 50 and the transducer unit 11 in a state in which the conduit unit 50 is coupled to the probe 41, holding unit 3 and transducer unit 11. FIG. 7 is a view illustrating a configuration in which the conduit unit 50 is detachably coupled to the probe 41, holding unit 3 and transducer unit 11. As illustrated in FIG. 6, in the state in which the conduit unit 50 is coupled to the probe 41, holding unit 3 and transducer unit 11, the liquid feed conduit 53 (liquid feed tube 51) and suction conduit 55 (suction tube 52) extend from the proximal direction to the distal direction through the space portion 36 formed in the inside of the connection member 32 and in the inside of the vibration damping member 33, and through the cavity portion 28 formed in the inside of the horn member 26 and in the inside of the elements-attached member 25. Further, the liquid feed conduit 53 (liquid feed tube 51) and suction conduit 55 (suction tube 52) extend toward the probe distal portion direction, up to the distal portion of the hollow portion 46 of the probe 41.

As illustrated in FIG. 5 to FIG. 7, the conduit unit 50 includes a cylindrical tube fixing member (liquid feed tube fixing member) 61 to which a proximal end of the liquid feed tube 51 is fixed by adhesion or the like. A cylindrical relay member 62 is attached to the tube fixing member 61. A tube fixing member (suction tube fixing member) 63 is fixed to the relay member 62. The suction tube 52 extends toward the probe proximal portion direction through the inside of the tube fixing member 61, and a proximal end of the suction tube 52 is fixed to the tube fixing member 63 by adhesion or the like.

In addition, in the conduit unit 50, a liquid feed relay path 65 is formed by the tube fixing member 61, relay member 62 and tube fixing member 63, and a suction relay path 66 is formed by the tube fixing member 63. A distal end of the liquid feed relay path 65 communicates with a proximal end of the liquid feed conduit 53, and a distal end of the suction relay path 66 communicates with a proximal end of the suction conduit 55. In addition, a connection mouthpiece (liquid feed mouthpiece) 67 and a connection mouthpiece (suction mouthpiece) 68 are fixed to the tube fixing member 63.

A female screw portion 71A is formed in the relay member 62. In addition, a male screw portion 71B is formed on the connection member 32 of the transducer unit 11. When the conduit unit 50 is coupled to the holding unit 3 and transducer unit 11, the liquid feed tube 51 (liquid feed conduit 53) and the suction tube 52 (suction conduit 55) are inserted through the space portion 36 and cavity portion 28 from the probe proximal portion direction side. Then, in the inside of the cylindrical case portion 5 of the holding unit 3, the liquid feed tube 51 (liquid feed conduit 53) and the suction tube 52 (suction conduit 55) are inserted into the hollow portion 46 of the probe 41 from the probe proximal portion direction side, and the female screw portion 71A of the relay member 62 is engaged with the male screw portion 71B of the connection member 32. Thereby, the conduit unit 50 is detachably coupled to the probe 41, holding unit 3 and transducer unit 11. Specifically, the female screw portion 71A of the relay member 62 and the male screw portion 71B of the connection member 32 serve as a conduit attachment/detachment portion which detachably couples the liquid feed conduit 53 and suction conduit 55 to the probe 41 and holding unit 3. In the meantime, by varying the fastening degree (loosening degree) between the female screw portion 71A and male screw portion 71B, the entirety of the conduit unit 50 (including the liquid feed conduit 53 and suction conduit 55) moves relative to the probe 41 in the longitudinal direction. Accordingly, by adjusting the fastening degree between the female screw portion 71A and male screw portion 71B, the positions of the ejection port 56 of liquid feed conduit 53 and the suction port 57 of suction conduit 55 relative to the probe 41 in the longitudinal direction are adjusted in the hollow portion 46 in the inside of the treatment section 42 (in the inside of the probe 41).

In addition, a female screw portion 72A is formed in the relay member 62, and a male screw portion 72B is formed on the tube fixing member 61. By engaging the female screw portion 72A with the male screw portion 72B, the relay member 62 is attached to the tube fixing member 61. In addition, by varying the fastening degree (loosening degree) between the female screw portion 72A and male screw portion 72B, the liquid feed conduit 53 moves relative to the suction conduit 55 in the longitudinal direction. Accordingly, by adjusting the fastening degree between the female screw portion 72A and male screw portion 72B, the position of the ejection port 56 of liquid feed conduit 53 relative to the suction port 57 of suction conduit 55 in the longitudinal direction is adjusted in the hollow portion 46 in the inside of the treatment section 42 (in the inside of the probe 41).

As illustrated in FIG. 1, one end of an external liquid feed tube 73 is connectable to the connection mouthpiece (liquid feed mouthpiece) 67 of the conduit unit 50. By the external liquid feed tube 73 being connected to the connection mouthpiece 67, the inside of the external liquid feed tube 73 communicates with a proximal end of the liquid feed relay path 65. In addition, one end of an external suction tube 75 is connectable to the connection mouthpiece (suction mouthpiece) 68 of the conduit unit 50. By the external suction tube 75 being connected to the connection mouthpiece 68, the inside of the external suction tube 75 communicates with a proximal end of the suction relay path 66.

The other end of the external liquid feed tube 73 is connected to a liquid feed source 76. The liquid feed source 76 includes a liquid feed actuation section 77 such as a liquid feed pump, and a liquid storage tank 78. The liquid feed actuation section 77 is electrically connected to the controller 18 of the energy source unit 15, and the actuation state of the liquid feed actuation section 77 is controlled by the controller 18. By the liquid feed actuation section 77 being actuated, a liquid, such as physiological saline, which is stored in the liquid storage tank 78, is supplied (fed) to the liquid feed conduit 53 through the inside of the external liquid feed tube 73 and the liquid feed relay path 65. In addition, in the liquid feed conduit 53, the liquid is supplied from the probe proximal portion direction to the probe distal portion direction.

The other end of the external suction tube 75 is connected to a suction source 81. The suction source 81 includes a suction actuation section 82 such as a suction pump, and a collection tank 83. The suction actuation section 82 is electrically connected to the controller 18 of the energy source unit 15, and the actuation state of the suction actuation section 82 is controlled by the controller 18. By the suction actuation section 82 being actuated, a flow (suction force) toward the suction source 81 occurs in the inside of the external suction tube 75, the suction relay path 66 and suction conduit 55. Specifically, by the suction actuation section 82 being actuated, a flow toward the probe proximal portion direction occurs in the suction conduit 55.

In the inside of the cylindrical case portion 5 (the inside of the holding unit 3), switch portions (not shown) are provided in association with the respective energy operation input buttons 9A to 9C. The respective switch portions are electrically connected to the controller 18 of the energy source unit 15 via corresponding signal path portions (not shown). Each signal path portion is formed of an electric conductor portion (not shown) of the transducer case 12, and an electric signal line (not shown) which extends in the inside of the cable 13. In addition, the energy operation input switch 10 is electrically connected to the controller 18 of the energy source unit 15. By an energy operation being input by each energy operation input button, 9A to 9C (that is, by each energy operation input button, 9A to 9C, being pressed), the corresponding switch portion is closed, and an electric signal is transmitted to the controller 18 through the corresponding signal path portion. In addition, by an energy operation being input by the energy operation input switch 10 (that is, by the energy operation input switch 10 being pressed), an electric signal is transmitted from the energy operation input switch 10 to the controller 18.

Based on the input of the energy operation (the transmitted electric signal), the controller 18 controls the output state of energy (ultrasonic electric power and high-frequency electric power) from the energy source unit 15. In addition, based on the input of the energy operation (the transmitted electric signal), the controller 18 controls the actuation state of the liquid feed actuation section 77 and the actuation state of the suction actuation section 82. For example, if an energy operation is input by the energy operation input button 9A, energy is output from the energy source unit 15 in a first output mode. If an energy operation is input by the energy operation input button 9B, energy is output from the energy source unit 15 in a second output mode. Besides, if an energy operation is input by the energy operation input button 9C, energy is output from the energy source unit 15 in a third output mode. If an energy operation is input by the energy operation input switch 10, energy is output from the energy source unit 15 in a fourth output mode. A description will be given later of the output states of energy from the energy source unit 15 in the first output mode to the fourth output mode, and the actuation state of the liquid feed actuation section 77 and the actuation state of the suction actuation section 82 in the respective output modes.

In addition, as illustrated in FIG. 1, the energy treatment system 1 includes a state setting unit 85. The state setting unit 85 is electrically connected to the controller 18 of the energy source unit 15. The state setting unit 85 is, for example, a touch panel, a button unit, etc.

FIG. 8 is a view illustrating the configuration of the state setting unit 85. As illustrated in FIG. 8, the state setting unit 85 includes liquid feed switch portions 86A to 86D, suction switch portions 87A to 87D, supply amount setting portions 88A to 88D, and supply amount display portions 89A to 89D. In each liquid feed switch portion, 86A to 86D, setting is executed as to whether the liquid feed actuation section 77 is actuated in the corresponding output mode (one of the first output mode to fourth output mode). For example, in the liquid feed switch portion 86A, setting is executed as to whether the liquid feed actuation section 77 is actuated in the first output mode. In each suction switch portion, 87A to 87D, setting is executed as to whether the suction actuation section 82 is actuated in the corresponding output mode (one of the first output mode to fourth output mode). For example, in the suction switch portion 87A, setting is executed as to whether the suction actuation section 82 is actuated in the first output mode. Besides, in each supply amount setting portion, 88A to 88D, when the liquid feed actuation section 77 is actuated in the corresponding output mode (one of the first output mode to fourth output mode), the supply amount (liquid feed amount) of liquid from the liquid feed actuation section 77 in the corresponding output mode is set. Then, the supply amount of liquid, which was set by each of the supply amount setting portions, 88A to 88D, is displayed on the corresponding supply amount display portion (corresponding one of 89A to 89D). For example, in the supply amount setting portion 88A, the supply amount of liquid from the liquid feed actuation section 77 in the first output mode, at a time when the liquid feed actuation section 77 is actuated in the first output mode, is set, and the set supply amount is displayed on the supply amount display portion 89A. Based on the setting in the state setting unit 85, the controller 18 controls the actuation state of the liquid feed actuation section 77 and the actuation state of the suction actuation section 82 in each of the first output mode to the fourth output mode.

As illustrated in FIG. 4, the treatment section 42 includes a probe distal wall 91 which forms the distal end of the probe 41. In addition, the outer surface of the treatment section 42 includes a treatment section distal surface 92 which is formed by the probe distal wall 91, and a treatment section side surface 93 which extends from the treatment section distal surface 92 toward the probe proximal portion direction. The treatment section distal surface 92 forms the distal end of the probe 41, and serves as a distal surface of the probe 41. In addition, the treatment section side surface 93 serves as an outer peripheral surface of the treatment section 42. In the present embodiment, the opening portion 47 of the hollow portion 46 is located on the treatment section distal surface 92 of the probe 41. In addition, the ejection port 56 of the liquid feed conduit 53 and the suction port 57 of the suction conduit 55 are located in the hollow portion 46 in the inside of the probe 41. Accordingly, the jet port 56 and suction port 57 are located on the probe proximal portion direction side with respect to the opening portion 47 of the hollow portion 46. Besides, the treatment section side surface 93 includes a probe-side counter-surface 95 which is opposed to the jaw 43. The probe-side counter-surface 95 faces toward the opening direction of the jaw 43 (the direction of arrow Y1 in FIG. 4). Incidentally, in FIG. 4, the direction of arrow Y2 is a closing direction of the jaw 43.

The suction actuation section 82 is actuated, and a flow (suction force) toward the probe proximal portion direction occurs in the suction conduit 55. Thereby, suction force F1 occurs from the outside of the probe 41 toward the suction conduit 55 through the opening portion 47 of the hollow portion 46 and the suction port 57. In addition, the liquid feed actuation section 77 is actuated, and a liquid is supplied toward the probe distal portion direction in the liquid feed conduit 53. Thereby, the liquid supplied in the hollow portion 46 is ejected from the ejection port 56 toward the probe distal portion direction side.

The probe distal wall 91 of the treatment section 42 is provided with a collision surface (circulation flow causing portion) 96. The collision surface 96 faces toward the probe proximal portion direction, and is opposed to at least a part of the ejection port 56 of the liquid feed conduit 53. Specifically, at least a part of the ejection port 56 is not opposed to the opening portion 47 of the hollow portion 46, and is opposed to the collision surface 96 of the probe distal wall 91. In this embodiment, the collision surface 96 is located on the probe distal portion direction side with respect to the ejection port 56 and suction port 57.

Since the collision surface 96 is opposed to at least a part of the ejection port 56, at least part of the liquid, which was ejected from the ejection port 56, collides with the collision surface 96 in the hollow portion 46. By the collision with the collision surface 96, the direction of the flow of liquid is changed to such a state that the liquid flows toward the probe proximal portion direction. Specifically, part of the liquid is caused to stay in the hollow portion 46 by the collision surface 96. When the suction actuation section 82 is actuated and suction force is occurring, part of the liquid ejected from the ejection port 56 flows toward the suction conduit 55 from the collision surface 96 through the suction port 57. Specifically, in the hollow portion 46, a flow (arrow X1 in FIG. 4) of liquid is formed toward the suction conduit 55 from the collision surface 96 through the suction port 57. In addition, in this embodiment, part of the liquid ejected from the ejection port 56 does not collide with the collision surface 96, and is ejected to the outside of the probe 41 through the opening portion 47 of the hollow portion 46 (arrow X2 in FIG. 4). Specifically, the actuation state of the liquid feed actuation section 77 and the actuation state of the suction actuation section 82 are controlled and the shapes, positions and dimensions of the collision surface 96 and opening portion 47 are designed, in such a state that part of the liquid ejected from the ejection port 56 is ejected to the outside of the probe 41 from the opening portion 47.

Next, the functions and advantageous effects of the energy treatment unit 30, energy treatment instrument 2 and energy treatment system 1 of the present embodiment will be described. When a treated target, such as a biological tissue, is treated by the energy treatment system 1, the conduit unit 50 is coupled to the holding unit 3 and transducer unit 11 by the conduit attachment/detachment portion (the female screw portion 71A of the relay member 62 and the male screw portion 71B of the connection member 32). Then, the cable 13 is connected to the energy supply unit 15. In addition, the conduit unit 50 is connected to the liquid feed source 76 by the external liquid feed tube 73, and the conduit unit 50 is connected to the suction source 81 by the external suction tube 75. In this state, the treatment section 42 and jaw 43 are inserted into the body.

For example, in a certain treatment, a treated target is disposed between the treatment section 42 and jaw 43, and the movable handle 7 is closed relative to the stationary handle 6. Thereby, the jaw 43 is closed relative to the treatment section 42, and the treated target is grasped between the treatment section 42 and jaw 43. In this state, an energy operation is input by the energy operation input button 9A, and energy is output from the energy source unit 15 in the first output mode. In the first output mode, ultrasonic electric power is supplied to the ultrasonic transducer 21 from the ultrasonic energy source 16, and ultrasonic vibration is caused by the ultrasonic transducer 21. Then, the caused vibration is transmitted to the treatment section 42 via the ultrasonic probe 41 (vibrating body unit 20). In addition, in the first output mode, high-frequency electric power is output from the high-frequency energy source 17. Then, the high-frequency electric power is supplied to the treatment section 42 through the probe-side electricity supply path P1, and the high-frequency electric power is supplied to the electric conductor portion (not shown) of the jaw 43 through the jaw-side electricity supply path P2. Thereby, the treatment section 42 and the electric conductor portion of the jaw 43 function as electrodes with mutually different electric potentials. In the state in which the treated target is grasped between the jaw 43 and treatment section 42, the treatment section 42 longitudinally vibrates, and thereby frictional heat occurs between the treatment section 42 and the treated target. By the frictional heat, the treated target is coagulated and, at the same time, cut. In addition, in the state in which the treated target is grasped between the jaw 43 and treatment section 42, the treatment section 42 and the electric conductor portion of the jaw 43 function as the electrodes. Thereby, a high-frequency current flows between the treatment section 42 and the electric conductor portion of the jaw 43 via the treated target. Thereby, the treated target is denatured, and coagulation is promoted.

Additionally, in another treatment, an energy operation is input by the energy operation input button 9B, and energy is output from the energy source unit 15 in the second output mode. In the second output mode, the high-frequency electric power is supplied to the treatment section 42 through the probe-side electricity supply path P1, and the high-frequency electric power is supplied to the electric conductor portion (not shown) of the jaw 43 through the jaw-side electricity supply path P2. Thereby, the treatment section 42 and the electric conductor portion of the jaw 43 function as electrodes with mutually different electric potentials, and a bipolar treatment is performed in which a high-frequency current is passed between the treatment section 42 and the electric conductor portion of the jaw 43 via the treated target. In the meantime, in the second output mode, no ultrasonic electric power is output from the ultrasonic energy source 16, nor does ultrasonic vibration occur.

Additionally, in another treatment, an energy operation is input by the energy operation input button 9C, and energy is output from the energy source unit 15 in the third output mode. In the third output mode, high-frequency electric power is supplied to the treatment section 42 through the probe-side electricity supply path P1, and high-frequency electric power is supplied to a counter-electrode plate (not shown) which is disposed outside the body. At this time, no high-frequency electric power is supplied to the electric conductor portion (not shown) of the jaw 43 through the jaw-side electricity supply path P2. Thereby, a monopolar treatment is performed in which a high-frequency current is passed between the treatment section 42 and the counter-electrode plate on the outside of the body via the treated target. In the meantime, in the third output mode, no ultrasonic electric power is output from the ultrasonic energy source 16, nor does ultrasonic vibration occur.

When the state setting unit 85 is set in standard setting (initial setting), neither the liquid feed actuation section 77 nor the suction actuation section 82 is actuated in each of the first output mode to the third output mode. However, by changing the setting from the standard state by the state setting unit 85, the liquid feed actuation section 77 can be actuated and the suction actuation section 82 can be actuated in each of the first output mode to the third output mode. In each of the first output mode to the third output mode, when the liquid feed actuation section 77 is actuated, the supply amount of liquid from the liquid feed actuation section 77 can be adjusted.

Additionally, aside from the energy operation input sections (9A to 9C, and 10), a liquid feed operation input section and a suction operation input section may be provided. The liquid feed operation input section and suction operation input section are, for example, operation input buttons which are provided on the energy treatment instrument 2, or footswitches which are separated bodies from the energy treatment instrument 2. In this case, by a liquid feed operation being input by the liquid feed operation input section, the liquid feed actuation unit 77 is actuated, and liquid is supplied to the liquid feed conduit 53. At this time, no energy is output from the energy source unit 15, nor is the suction actuation unit 82 actuated. In short, only the ejecting of liquid from the ejection port 56 is performed. Besides, by a suction operation being input by the suction operation input section, the suction actuation unit 82 is actuated, and a flow toward the probe proximal portion direction occurs in the suction conduit 55. At this time, no energy is output from the energy source unit 15, nor is the liquid feed actuation unit 77 actuated. In short, only the suction through the suction port 57 is performed.

Additionally, in another treatment, an energy operation is input by the energy operation input switch 10, and energy is output from the energy source unit 15 in the fourth output mode. In the fourth output mode, ultrasonic electric power is supplied to the ultrasonic transducer 21 from the ultrasonic energy source 16, and ultrasonic vibration is caused by the ultrasonic transducer 21. Then, the caused vibration is transmitted to the treatment section 42 via the ultrasonic probe 41 (vibrating body unit 20). When the state setting unit 85 is set in the standard setting (initial setting), the liquid feed actuation section 77 is actuated and the suction actuation section 82 is actuated in the fourth output mode. Thus, liquid is supplied toward the probe distal portion direction in the liquid feed conduit 53, and the liquid, which has been supplied toward the probe distal portion direction, is ejected from the ejection port 56 in the hollow portion 46. In addition, part of the liquid ejected from the ejection port 56 is ejected from the opening portion 47 of the hollow portion 46 to the outside of the probe 41 (arrow X2 in FIG. 4).

In the state in which the treatment section 42 (probe 41) is longitudinally vibrating at high speed, the liquid is supplied to the vicinity of the treatment section distal surface 92, and thereby cavitation occurs near the treatment section distal surface 92. By the cavitation occurring in the state in which the treatment section distal surface 92 is opposed to the treated target, the treated target is crushed and emulsified. In the meantime, by the cavitation, only a biological tissue with low resiliency, such as hepatic cells, is selectively crushed, and a biological tissue with resiliency, such as a blood vessel, is not crushed.

In the present embodiment, liquid is supplied through the liquid feed conduit 53 which extends in the inside of the hollow portion 46, and the supplied liquid is ejected from the ejection port 56 in the hollow portion 46. Then, part of the liquid ejected from the ejection port 56 is jetted to the outside of the probe 41 from the hollow portion 46 through the opening portion 47 which is located on the treatment section distal surface 92. Thus, the liquid supplied from the liquid feed source 76 does not drop, for example, from the proximal portion of the treatment section 42 to a region other than the treated target, and the liquid is properly supplied to the vicinity of the treatment section distal surface 92 on the outside of the probe 41. Thereby, cavitation properly occurs, and the treated target can properly be crushed and emulsified.

Additionally, the ejection port 56 of the liquid feed conduit 53 is located on the probe proximal portion direction side with respect to the opening portion 47. Accordingly, part of the liquid, which has been ejected from the ejection port 56 to the probe distal portion direction side in the hollow portion 46, is properly ejected from the opening portion 47 to the outside of the probe 41. Therefore, liquid can exactly be supplied to the vicinity of the treatment section distal surface 92 on the outside of the probe 41, and the treatment performance of the treatment of crushing and emulsifying the treated target can be enhanced.

FIG. 9 illustrates a variation with time of longitudinal vibration at a certain position of the treatment section 42 (at a position different from a node position of longitudinal vibration) in a state in which energy is being output in the fourth output mode from the energy source unit 15. As illustrated in FIG. 9, in the state in which energy is being output in the fourth output mode from the energy source unit 15, the amplitude of the treatment section 42 is not constant with the passing of time. Specifically, in the fourth output mode, the ultrasonic electric power, which is output from the ultrasonic energy source 16, is modulated by the controller 18. For example, the modulation is executed by varying, with the passing of time, the amplitude, cycle, etc. of electric current (AC current) which is supplied to the ultrasonic transducer 21. By the ultrasonic electric power being modulated, the amplitude of longitudinal vibration varies with time, for example, in such a state that vibration occurs with a first amplitude V1, or vibration occurs with a second amplitude V2 that is less than the first amplitude V1, at a certain position of the treatment section 42. In addition, by the ultrasonic electric power being modulated, for example, the cycle of longitudinal vibration varies with time. Besides, in the case where the amplitude of longitudinal vibration varies with time in the state in which vibration occurs with the first amplitude V1 or in the state in which vibration occurs with the second amplitude V2, the ratio of a time T1, during which vibration occurs with the first amplitude V1, in a fixed time ΔT, or the ratio of a time T2, during which vibration occurs with the amplitude V2, in the fixed time ΔT, is defined as "duty ratio". For example, the duty ratio varies with time by the ultrasonic electric power being modulated.

A blood vessel or the like extends in the inside of hepatic cells, which are crushed by cavitation. By modulating the ultrasonic electric power and varying with time the vibration state of the treatment section 42, damage to the blood vessel extending in the inside of hepatic cells can effectively be prevented, even when the hepatic cells are crushed and emulsified by the cavitation.

Additionally, in the fourth output mode, since the suction actuation section 82 is actuated, a flow toward the probe proximal portion direction occurs in the suction conduit 55. Thereby, suction force (arrow F1 in FIG. 4) acts toward the suction conduit 55 from the outside of the probe 41 through the opening portion 47 of the hollow portion 46 and the suction port 57. Thereby, the treated target, which was shattered and emulsified by the cavitation, is sucked toward the suction conduit 55 through the opening portion 47 and suction port 57. Then, the sucked object (crushed and emulsified treated target) is sucked in the suction conduit 55 toward the probe proximal portion direction, and the sucked object is collected in the collection tank 83 of the suction source 81.

In the present embodiment, the opening portion 47 of the hollow portion 46 is provided on the treatment section distal surface 92 which is different from the probe-side countersurface 95 that is opposed to the jaw 43. Thus, the opening portion 47 is not closed by the jaw 43. Therefore, the crushed and emulsified treated target (sucked object) can be sucked into the suction conduit 55 through the opening portion 47.

Additionally, the suction port 57 of the suction conduit 55 is located on the probe proximal portion direction side with respect to the opening portion 47. Accordingly, the sucked object, which was sucked in the hollow portion 46 from the opening portion 47, is properly sucked into the suction conduit 55 from the suction port 57, and the suction performance of the crushed and emulsified treated target (sucked object) can be enhanced.

Additionally, by using the energy (ultrasonic vibration, high-frequency electric power) in the treatment, heat, such as the above-described frictional heat, due to the ultrasonic vibration occurs in the probe 41. Thus, the temperature of the probe 41 (in particular, treatment section 42) becomes high due to the produced heat, and also the temperature of the suction conduit 55, which extends in the hollow portion 46 in the inside of the probe 14, becomes high. By the high temperature of the suction conduit 55, the sucked object, which is sucked through the suction conduit 55, is burnt, and the burnt sucked object tends to be easily adhere to the inner peripheral surface of the suction conduit 55 (the inner peripheral surface of the suction tube 52). By the sucked object (crushed biological tissue or the like) adhering to the inner peripheral surface of the suction conduit 55, clogging occurs in the suction conduit 55.

Taking the above into account, in the present embodiment, the probe distal wall 91 is provided with the collision surface 96, and the collision surface 96 is opposed to at least a part of the ejection port 56. Thus, in the hollow portion 46, part of the liquid ejected from the ejection port 56 collides with the collision surface 96, and the direction of the flow of liquid is changed to such a state that the liquid flows toward the probe proximal portion direction. Thereby, in the hollow portion 46, a flow (arrow X1 in FIG. 4) of liquid is formed toward the suction conduit 55 from the collision surface 96 through the suction port 57. In addition, the liquid coming in from the suction port 57 moves in the suction conduit 55 from the probe distal portion direction to the probe proximal portion direction. In the meantime, part of the liquid ejected from the ejection port 56 is not caused to collide with the collision surface 96, flows into the suction conduit 55 through the suction port 57, and moves in the suction conduit 55 from the probe distal portion direction to the probe proximal portion direction. Accordingly, in the state in which the liquid is ejected from the ejection port 56, the liquid that has collided with the collision surface 96 flows in from the suction port 57, and/or the liquid, without colliding with the collision surface 96, flows in from the suction port 57 as such, and a flow of liquid toward the probe proximal portion direction is formed over the entire length of the suction conduit 55 (i.e. from the suction port 57 to the proximal end of the suction conduit 55). Since the liquid flows toward the probe proximal portion direction from the suction port 57 (distal end) to the proximal end in the suction conduit 55, the sucked object is not easily burnt in the suction conduit 55. Thereby, the adhesion of the sucked object to the inner peripheral surface of the suction conduit 55 is prevented, and the occurrence of clogging in the suction conduit 55 can effectively be prevented.

Additionally, in this embodiment, the collision surface 96 is located on the probe distal portion direction side with respect to the ejection port 56 of the liquid feed conduit 53 and the suction port 57 of the suction conduit 55. In addition, the cross section of the liquid feed conduit 53, which is perpendicular to the longitudinal axis C, has a cylindrical shape surrounding the outer peripheral side of the suction conduit 55, and the suction port 57 of the suction conduit 55 is located on the probe distal portion direction side with respect to the ejection port 56 of the liquid feed conduit 53. By this configuration, at least part of the liquid ejected from the ejection port 56 can exactly be caused to collide with the collision surface 96. In addition, the liquid that has collided with the collision surface 96 can exactly be caused to flow into the suction conduit 55 through the suction port 57.

Additionally, in this embodiment, the conduit unit 50 is detachable from the probe 41 and holding unit 3. Thus, even if clogging occurs in the suction conduit 55, the conduit unit 50 can be detached from the probe 41 and sucked object, which is clogged in the suction conduit 55, can be removed. Furthermore, the conduit unit 50, in which clogging occurred in the suction conduit 55, can be replaced with a new conduit unit 50. Specifically, in the energy treatment instrument 2 of this embodiment, even if clogging occurs in the suction conduit 55, it is easy to deal with the clogging.

Modifications

Figure 10:
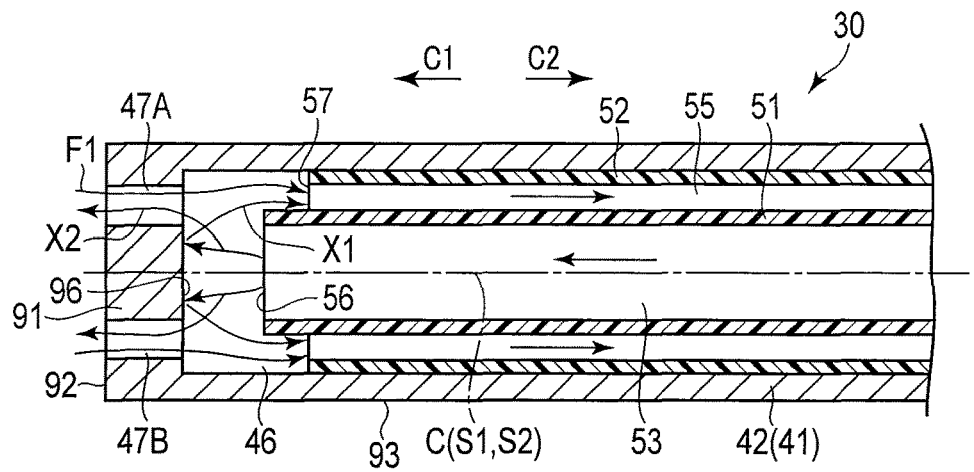
FIG. 10 is a cross-sectional view which schematically illustrates the configuration of a treatment section of a probe and a distal portion of a conduit unit according to a first modification.

In the first embodiment, the cross section of the liquid feed conduit 53, which is perpendicular to the longitudinal axis C, has the cylindrical shape surrounding the outer peripheral side of the suction conduit 55, but the restriction to this is unnecessary. In addition, in the first embodiment, only one opening portion 47 of the hollow portion 46 is provided, but the restriction to this is unnecessary. For example, a first modification will be described with reference to FIG. 10 and FIG. 11. FIG. 10 illustrates the configuration of a treatment section 42 and a distal portion of a conduit unit 50 according to this modification, and FIG. 11 illustrates a treatment section distal surface 92 of the treatment section 42.

Figure 11:
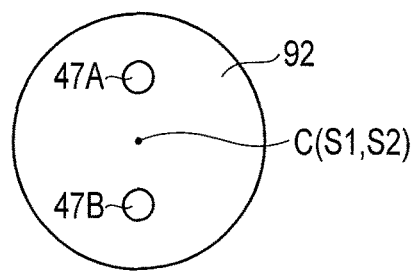
FIG. 11 is a schematic view of a treatment section distal surface of the treatment section according to the first modification, as viewed from the distal direction side.

As illustrated in FIG. 10 and FIG. 11, in the present modification, the liquid feed tube 51 is inserted through the inside of the suction tube 52. Thus, the suction conduit 55 extends between the inner peripheral surface of the suction tube 52 and the outer peripheral surface of the liquid feed tube 51. In this modification, too, the conduit axis (liquid feed conduit axis) S1 of the liquid feed conduit 53 and the conduit axis (suction conduit axis) S2 of the suction conduit 55 are coaxial with the longitudinal axis C. By adopting the above configuration, the cross section of the liquid feed conduit 53, which is perpendicular to the longitudinal axis C, has a circular shape about the longitudinal axis C (conduit axis S1), and the cross section of the suction conduit 55, which is perpendicular to the longitudinal axis C, has a cylindrical (circular cylindrical) shape surrounding the outer peripheral side of the liquid feed conduit 53. In addition, in this modification, the ejection port 56 of the liquid feed conduit 53 is located on the probe distal portion direction side with respect to the suction port 57 of the suction conduit 55.

In this modification, too, the probe distal wall 91 of the treatment section 42 is provided with a collision surface 96. The collision surface 96 faces toward the probe proximal portion direction, and is opposed to at least a part of the ejection port 56 of the liquid feed conduit 53. In addition, the collision surface 96 is located on the probe distal portion direction side with respect to the ejection port 56 and suction port 57. Thus, in the hollow portion 46, at least part of the liquid, which was ejected from the ejection port 56, collides with the collision surface 96. Thereby, in the hollow portion 46, a flow (arrow X1 in FIG. 10) is formed, by which at least part of the liquid ejected from the ejection port 56 flows toward the suction conduit 55 from the collision surface 96 through the suction port 57.

Additionally, in this modification, the longitudinal axis C, which is coaxial with the conduit axis S1 of the liquid feed conduit 53, passes through the collision surface 96. It is thus easy to cause at least part of the liquid ejected from the ejection port 56 to collide with the collision surface 96.

As illustrated in FIG. 11, in this modification, two (plural) opening portions 47A and 47B are provided on the treatment section distal surface 92. The hollow portion 46 is open to the outside of the probe 41 at the opening portions 47A and 47B. The opening portions 47A and 47B are located at positions on the treatment section distal surface 92, where the longitudinal axis C (conduit axis S1 of the liquid feed conduit 53) does not pass. In addition, in this modification, the opening portions 47A and 47B are disposed to be spaced apart from each other over about 180° around the longitudinal axis C.

Like the first embodiment, the treated target (biological tissue), which was crushed and emulsified by cavitation, is sucked in the hollow portion 46 through the opening portions 47A and 47B. In this modification, since the opening portions 47A and 47B are located at positions on the treatment section distal surface 92, where the conduit axis S1 of the liquid feed conduit 53 does not pass, the sucked object (biological tissue or the like) coming into the hollow portion 46 is effectively prevented from flowing into the liquid feed conduit 53 from the ejection port 56.

Additionally, when the treated target is coagulated and, at the same time, cut by ultrasonic vibration, there is a case in which, after the treatment section 42 and jaw 43 are pierced into the biological tissue (hepatic cells), the jaw 43 is closed relative to the treatment section 42 and the grasped treated target is treated. In this treatment, in the state in which the treatment section 42 is pierced into the treated target, the treated target is grasped between the treatment section 42 and jaw 43, and the grasped biological tissue is coagulated and, at the same time, cut by ultrasonic vibration. In this modification, since the opening portions 47A and 47B are located at positions on the treatment section distal surface 92, where the conduit axis S1 of the liquid feed conduit 53 does not pass, the biological tissue is effectively prevented from entering the liquid feed conduit 53 from the ejection port 56, when the treatment section 42 is pierced into the biological tissue (hepatic cells) in the treatment.

Figure 12:
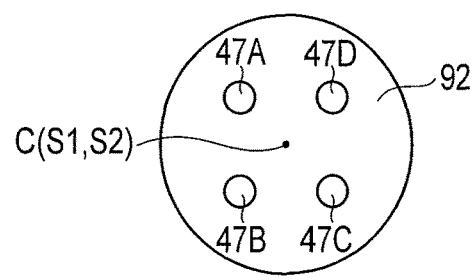
FIG. 12 is a schematic view of a treatment section distal surface of a treatment section according to a second modification, as viewed from the distal direction side.

Additionally, as illustrated in FIG. 12 as a second modification, four opening portions 47A to 47D may be provided on the treatment section distal surface 92. In the present modification, like the first modification, in the hollow portion 46, the liquid feed tube 51 is inserted through the suction tube 52, and the conduit axis S1 of the liquid feed conduit 53 is coaxial with the longitudinal axis C. Each opening portion, 47A to 47D, is disposed to be spaced apart from neighboring opening portions (two of 47A to 47D) over about 90° around the longitudinal axis C. In this modification, like the first modification, the longitudinal axis C, which is coaxial with the conduit axis S1 of the liquid feed conduit 53, passes through the collision surface 96. Thus, the collision surface 96 is opposed to at least a part of the ejection port 56 of the liquid feed conduit 53. In addition, like the first modification, the opening portions 47A top 47D are located at positions on the treatment section distal surface 92, where the longitudinal axis C (conduit axis S1) does not pass.

Figure 13:
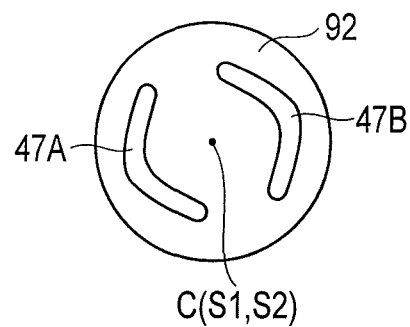
FIG. 13 is a schematic view of a treatment section distal surface of a treatment section according to a third modification, as viewed from the distal direction side.

Additionally, as illustrated in FIG. 13 as a third modification, two opening portions 47A and 47B, which are formed in slit shapes extending in a direction around the longitudinal axis C, may be provided on the treatment section distal surface 92. In the present modification, like the first modification, in the hollow portion 46, the liquid feed tube 51 is inserted through the suction tube 52, and the conduit axis S1 of the liquid feed conduit 53 is coaxial with the longitudinal axis C. Each opening portion, 47A, 47B, extends over an angular range of about 120° around the longitudinal axis C. The opening portions 47A and 47B are located to be spaced apart from each other over about 180°. In this modification, like the first modification, the longitudinal axis C, which is coaxial with the conduit axis S1 of the liquid feed conduit 53, passes through the collision surface 96. Thus, the collision surface 96 is opposed to at least a part of the ejection port 56 of the liquid feed conduit 53. In addition, like the first modification, the opening portions 47A and 47B are located at positions on the treatment section distal surface 92, where the longitudinal axis C (conduit axis S1) does not pass.

Figure 14:
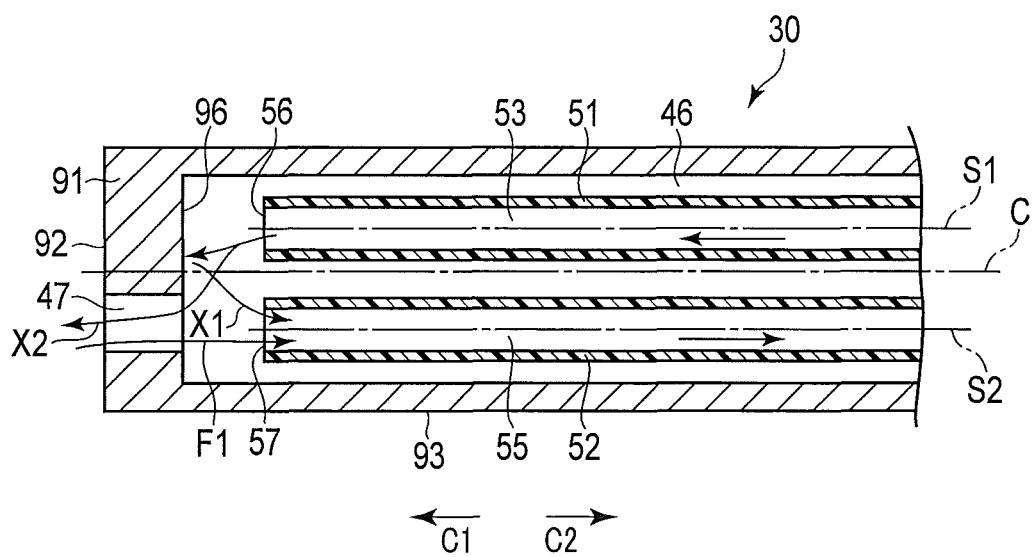
FIG. 14 is a cross-sectional view which schematically illustrates the configuration of a treatment section of a probe and a distal portion of a conduit unit according to a fourth modification.

Additionally, in the above-described embodiment, etc., one of the liquid feed tube 51 and suction tube 52 is inserted through the other of the liquid feed tube 51 and suction tube 52. However, the restriction to this is unnecessary. For example, as illustrated in FIG. 14 as a fourth modification, in the hollow portion 46, the suction tube 52 extends in the outside of the liquid feed tube 51, and the liquid feed tube 51 extends in the outside of the suction tube 52. Accordingly, the conduit axis S1 of the liquid feed conduit 53 is not coaxial with the conduit axis S2 of the suction conduit 55. In addition, in this modification, the conduit axis S1 of the liquid feed conduit 53 and the conduit axis S2 of the suction conduit 55 are not coaxial with the longitudinal axis C.

In this modification, too, the opening portion 47 of the hollow portion 46 is formed on the treatment section distal surface 92. The conduit axis S2 of the suction conduit 55 passes through the opening portion 47. Thus, the treated target, which was crushed and emulsified by the cavitation, is made to easily flow into the suction conduit 55, by the suction force (arrow F1 in FIG. 14) acting toward the suction conduit 55 from the outside of the probe 41 through the opening portion 47 and suction port 57.

Additionally, in this modification, too, the probe distal wall 91 of the treatment section 42 is provided with the collision surface 96. The collision surface 96 faces toward the probe proximal portion direction, and is opposed to at least a part of the ejection port 56 of the liquid feed conduit 53. In addition, the collision surface 96 is located on the probe distal portion direction side with respect to the ejection port 56 and suction port 57. Thus, in the hollow portion 46, at least part of the liquid, which was ejected from the ejection port 56, collides with the collision surface 96. Thereby, in the hollow portion 46, a flow (arrow X1 in FIG. 14) is formed, by which at least part of the liquid ejected from the ejection port 56 flows toward the suction conduit 55 from the collision surface 96 through the suction port 57.

Additionally, the conduit axis S1 of the liquid feed conduit 53 passes through the collision surface 96, and the opening portion 47 is located at a position on the treatment section distal surface 92, where the conduit axis S1 of the liquid feed conduit 53 does not pass. Thus, the sucked object (crushed and emulsified biological tissue or the like) coming into the hollow portion 46 is effectively prevented from flowing into the liquid feed conduit 53 from the ejection port 56.

Additionally, in the above-described embodiment, etc., the opening portion (47; 47A, 47B; 47A to 47D) of the hollow portion 46 is provided on the treatment section distal surface 92, but the restriction to this is unnecessary. For example, as illustrated in FIG. 15 as a fifth modification, an opening portion 97, which is open to the outside of the hollow portion 46, may be provided on the treatment section side surface 93. In this modification, no opening portion is provided on the treatment section distal surface 92. The opening portion 97 is located in the distal portion of the treatment section 42, and is located, in this modification, in a part facing toward the closing direction (the direction of arrow Y2 in FIG. 15) of the jaw 43. Accordingly, the opening portion 97 is located in a position on the treatment section side surface 93, which is other than the probe-side counter-surface 95. Thus, the opening portion 47 is not closed by the jaw 43. Accordingly, the treated target (sucked object), which was crushed and emulsified, can properly be sucked into the suction conduit 55 through the opening portion 47.

In the present modification, like the fourth modification, in the hollow portion 46, the suction tube 52 extends in the outside of the liquid feed tube 51, and the liquid feed tube 51 extends in the outside of the suction tube 52. In addition, in this modification, the position of the ejection port 56 at the distal end of the liquid feed conduit 53 agrees with the position of a proximal end of the opening portion 97 in the longitudinal direction which is parallel to the longitudinal axis C. Besides, the position of the suction port 57 at the distal end of the suction conduit 55 agrees with the position of the proximal end of the opening portion 97 in the longitudinal direction. In the meantime, the ejection port 56 and suction port 57 may be located on the probe proximal portion direction side with respect to the proximal end of the opening portion 97.

In this modification, too, the probe distal wall 91 of the treatment section 42 is provided with the collision surface 96. The collision surface 96 faces toward the probe proximal portion direction, and is opposed to the entirety (at least a part) of the ejection port 56 of the liquid feed conduit 53. In addition, the collision surface 96 is located on the probe distal portion direction side with respect to the ejection port 56 and suction port 57. Thus, in the hollow portion 46, at least part of the liquid, which was ejected from the ejection port 56, is not ejected to the outside of the probe 41 from the opening portion 97, and collides with the collision surface 96. Thereby, in the hollow portion 46, a flow (arrow X1 in FIG. 15) is formed, by which at least part of the liquid ejected from the ejection port 56 flows toward the suction conduit 55 from the collision surface 96 through the suction port 57.

Additionally, in this modification, too, liquid is supplied through the liquid feed conduit 53 which extends in the inside of the hollow portion 46, and the supplied liquid is ejected from the ejection port 56 in the hollow portion 46. Then, part of the liquid ejected from the ejection port 56 is ejected to the outside of the probe 41 (arrow X2 in FIG. 15) from the hollow portion 46 through the opening portion 97 which is located on the treatment section side surface 93. The opening portion 97 is located at a probe-distal-portion-direction-side part (a distal portion of the treatment section side surface 93) of the treatment section 42. Thus, the liquid supplied from the liquid feed source 76 does not drop, for example, from the proximal portion of the treatment section 42 to a region other than the treated target, and the liquid is properly supplied to the vicinity of the treatment section distal surface 92 on the outside of the probe 41.

Additionally, as illustrated in FIG. 16 and FIG. 17 as a sixth modification, two (plural) opening portions 97A and 97B may be provided on the treatment section side surface 93. In this modification, like the fifth modification, no opening portion is provided on the treatment section distal surface 92. In addition, in this modification, like the fourth modification and fifth modification, in the hollow portion 46, the suction tube 52 extends in the outside of the liquid feed tube 51, and the liquid feed tube 51 extends in the outside of the suction tube 52. The opening portions 97A and 97B are located at angular positions spaced apart from each other over about 180° around the longitudinal axis C. The positions of the opening portions 97A and 97B agree in the longitudinal direction. In addition, the position of the ejection port 56 at the distal end of the liquid feed conduit 53 agrees with the position of a proximal end of the opening portion 97A (a proximal end portion of the opening portion 97B) in the longitudinal direction which is parallel to the longitudinal axis C. Besides, the position of the suction port 57 at the distal end of the suction conduit 55 agrees with the position of the proximal end of the opening portion 97A in the longitudinal direction. In the meantime, the ejection port 56 and suction port 57 may be located on the probe proximal portion direction side with respect to the proximal end of the opening portion 97A (the proximal end portion of the opening portion 97B).

In this modification, the opening portions 97A and 97B are located at positions on the treatment section side surface 93 which is other than the probe-side counter-surface 95. Incidentally, it should suffice if at least one of the opening portions 97A and 97B is located at a position on the treatment section side surface 93 which is other than the probe-side counter-surface 95. Thereby, at least one of the opening portions 97A and 97B is not closed by the jaw 43. In FIG. 16, a vertically upward direction relative to the drawing sheet is the opening direction of the jaw 43. In addition, FIG. 17 illustrates a cross section which extends through the opening portions 97A and 97B and is perpendicular to the longitudinal axis C. The direction of arrow Y1 is the opening direction of the jaw 43, and the direction of arrow Y2 is the closing direction of the jaw 43.

Additionally, in this modification, a plurality of opening portions 97A and 97B are provided. Thus, even if clogging occurs in one of the opening portions 97A and 97B due to a crushed tissue or the like, suction into the suction conduit 55 is performed and liquid supplied through the liquid feed conduit 53 is ejected to the outside of the probe 41, through the other of the opening portions 97A and 97B (the opening portion 97A or 97B in which no clogging occurs).

Additionally, in this modification, in the opening portion (first opening portion) 97A, the distance from the suction port 57 of the suction conduit 55 is less than the distance from the ejection port 56 of the liquid feed conduit 53. Specifically, compared to the ejection port 56, the suction port 57 is closer to the opening portion 97A. Thus, the suction force (arrow F1 in FIG. 16) toward the suction conduit 55 from the outside of the probe 41 through the opening portion 97A and suction port 57 is greater than the suction force toward the suction conduit 55 from the outside of the probe 41 through the opening portion 97B. Accordingly, the opening portion 97A is mainly used as an opening for causing sucked object, such as a crushed treated target, to flow into the hollow portion 46.

On the other hand, in the opening portion (second opening portion) 97B, the distance from the ejection port 56 of the liquid feed conduit 53 is less than the distance from the suction port 57 of the suction conduit 55. Specifically, compared to the suction port 57, the ejection port 56 is closer to the opening portion 97B. Thus, in the hollow portion 45, part of liquid ejected from the ejection port 56 is ejected to the outside of the probe 41, mainly through the opening portion 97B (arrow X2 in FIG. 16). Accordingly, the opening portion 97B is mainly used as an opening for ejecting liquid to the outside of the probe 41 and supplying liquid to the vicinity of the treatment section distal surface 92.

As described above, in the present modification, in addition to the opening portion (first opening portion) 97A for causing sucked object from the outside of the probe 41 to flow into the hollow portion 46, there is provided the opening portion (second opening portion) 97B for ejecting liquid to the outside of the probe 41. In addition, the opening portions 97A and 97B are located to be spaced apart from each other. Thus, the supply performance of liquid to the vicinity of the treatment section distal surface 92 is enhanced, and the suction performance through the suction conduit 55 is also enhanced.

Additionally, as illustrated in FIG. 18 as a seventh modification, four (plural) opening portions 97A to 97D may be provided on the treatment section side surface 93. In the present modification, like the fifth modification, no opening portion is provided on the treatment section distal surface 92. In addition, in this modification, like the fourth modification and fifth modification, in the hollow portion 46, the suction tube 52 extends in the outside of the liquid feed tube 51, and the liquid feed tube 51 extends in the outside of the suction tube 52. The positions of the opening portions 97A to 97D agree in the longitudinal direction. In addition, each of the opening portions 97A to 97D is disposed to be spaced apart from neighboring opening portions (corresponding two of 97A to 97D) over about 90° around the longitudinal axis C. In this modification, only the opening portion 97D is located on the probe-side counter-surface 95 which is opposed to the jaw 43, and the opening portions 97A to 97C are located at positions on the treatment section side surface 93 which is other than the probe-side counter-surface 95.

Additionally, as illustrated in FIG. 19 as an eighth modification, two (plural) opening portions 97A and 97B may be provided on the treatment section side surface 93, and the opening portions 97A and 97B may be disposed apart from each other in the longitudinal direction. The opening portion (first opening portion) 97A is located on the probe distal portion direction side with respect to the opening portion (second opening portion) 97B. Compared to the ejection port 56, the suction port 57 is located closer to the opening portion 97A. Compared to the suction port 57, the ejection port 56 is located closer to the opening portion 97B. Accordingly, sucked object flows into the hollow portion 46 mainly through the opening portion 97A, and the liquid is ejected to the outside of the probe 41 mainly through the opening portion 97B. In the present modification, the opening portions 97A and 97B are disposed to be spaced apart from each other over about 180° around the longitudinal axis C. However, it should suffice if the opening portions 97A and 97B are located at angular positions spaced apart from each other around the longitudinal axis C. For example, the opening portions 97A and 97B may be located to be spaced apart from each other over about 90° around the longitudinal axis C. In addition, at least one of the opening portions 97A and 97B is located at a position on the treatment section side surface 93 which is other than the probe-side countersurface 95.

In the present modification, the positions of the ejection port 56 of the liquid feed conduit 53 and the suction port 57 of the suction conduit 55 agree with the position of the proximal end of the opening portion 97B in the longitudinal direction. However, it should suffice if the position of the suction port 57 agrees with the position of the proximal end of the opening portion (first opening portion) 97A in the longitudinal direction, or is located on the probe proximal portion direction side with respect to the opening portion 97A. In addition, it should suffice if the position of the ejection port 56 agrees with the position of the proximal end of the opening portion (second opening portion) 97B in the longitudinal direction, or is located on the probe proximal portion direction side with respect to the opening portion 97B.

Additionally, as illustrated in FIG. 20 as a ninth modification, two opening portions 47A and 47B may be provided on the treatment section distal surface 92, and two opening portions 97A and 97B may be provided on the treatment section side surface 93. The opening portions 47A and 47B are provided on the treatment section distal surface 92 at the same positions and with the same shapes as in the first modification (see FIG. 10 and FIG. 11). In addition, the opening portions 97A and 97B are provided on the treatment section side surface 93 at the same positions and with the same shapes as in the sixth modification (see FIG. 16 and FIG. 17). Further, in this modification, like the first modification, the liquid feed tube 51 is inserted through the suction tube 52, and the conduit axis S1 of the liquid feed conduit 53 is coaxial with the longitudinal axis C. Besides, like the first modification, the opening portions 47A and 47B are located at positions on the treatment section distal surface 92, where the conduit axis S1 (longitudinal axis C) does not pass, and the conduit axis S1 passes through the collision surface 96.

In the present modification, the position of the suction port 57 at the distal end of the suction conduit 55 agrees with the position of the proximal end of the opening portion 97A (the proximal end of the opening portion 97B) in the longitudinal direction, or is located on the probe proximal portion direction side with respect to the opening portion 97A. In addition, the position of the ejection port 56 at the distal end of the liquid feed conduit 53 is located on the probe distal portion direction side with respect to the opening portion 97A, and is located on the probe proximal portion direction side with respect to the opening portions 47A and 47B. Accordingly, in this modification, sucked object flows into the hollow portion 46 mainly through the opening portions 97A and 97B (arrow F1 in FIG. 20), and liquid is ejected to the outside of the probe 41 mainly from the opening portions 47A and 47B (arrow X2 in FIG. 20).

Additionally, in a tenth modification illustrated in FIG. 21, an opening portion 47 is provided on the treatment section distal surface 92, and two opening portions 97A and 97B are provided on the treatment section side surface 93. The opening portion 47 is provided on the treatment section distal surface 92 at the same position and with the same shape as in the fourth modification (see FIG. 14). In addition, the opening portions 97A and 97B are provided on the treatment section side surface 93 at the same positions and with the same shapes as in the sixth modification (see FIG. 16 and FIG. 17). Further, in this modification, like the fourth modification, the liquid feed tube 51 extends in the outside of the suction tube 52, and the suction tube 52 extends in the outside of the liquid feed tube 51. Besides, like the fourth modification, the opening portion 47 is located at a position on the treatment section distal surface 92, where the conduit axis S1 of the liquid feed conduit 53 does not pass, and the conduit axis S1 passes through the collision surface 96.

Additionally, in the above-described embodiment, etc., although both the liquid feed tube 51 and the suction tube 52 extend in the hollow portion 46, the restriction to this is unnecessary. For example, in an eleventh modification illustrated in FIG. 22, only the suction tube 52 extends in the hollow portion 46, and no liquid feed tube is provided. In this modification, a liquid feed conduit 53 is formed between the outer peripheral surface of the suction tube 52 and the inner peripheral surface of the probe 41. Accordingly, a ejection port 56 of the liquid feed conduit 53 is formed on the outer peripheral side of the distal end of the suction tube 52. In this modification, too, the probe distal wall 91 of the treatment section 42 is provided with a collision surface 96, and the collision surface 96 faces toward the probe proximal portion direction, and is opposed to at least a part of the ejection port 56 of the liquid feed conduit 53.

Additionally, for example, in a twelfth modification illustrated in FIG. 23, only the liquid feed tube 51 extends in the hollow portion 46, and no suction tube is provided. In this modification, a suction conduit 55 is formed between the outer peripheral surface of the liquid feed tube 51 and the inner peripheral surface of the probe 41. Accordingly, a suction port 57 of the suction conduit 55 is formed on the outer peripheral side of the distal end of the liquid feed tube 51. In this modification, too, the probe distal wall 91 of the treatment section 42 is provided with a collision surface 96, and the collision surface 96 faces toward the probe proximal portion direction, and is opposed to at least a part of the ejection port 56 of the liquid feed conduit 53.

Additionally, for example, in a 13th modification illustrated in FIG. 24, communication portions 101A and 101B are provided for establishing communication between the liquid feed conduit 53 and suction conduit 55 on the probe proximal portion direction side with respect to the ejection port 56 and suction port 57. In this modification, like the first embodiment, the suction tube 52 is inserted through the liquid feed tube 51. In addition, the opening portion 47 is provided on the treatment section distal surface 92 at the same position and with the same shape as in the first embodiment (see FIG. 4).

In the present modification, part of the liquid supplied from the liquid feed actuation section 77 (liquid feed source 76) flows from the liquid feed conduit 53 into the suction conduit 55 through the communication portions 101A and 101B (arrow X3 in FIG. 24). However, at least part of the liquid supplied from the liquid feed actuation section 77 to the liquid feed conduit 53 does not flow into the suction conduit 55 from the communication portions 101A and 101B, and is supplied to the ejection port 56. Then, in the hollow portion 46, the liquid supplied to the ejection port 56 is ejected toward the probe distal portion direction side from the ejection port 56. Specifically, the actuation states of the liquid feed actuation section 77 and suction actuation section 82 are controlled by the controller 18, in such a state that at least part of the liquid supplied from the liquid feed actuation section 77 does not flow into the suction conduit 55 from the communication portions 101A and 101B, and is ejected from the ejection port 56 in the hollow portion 46.

At least part of the liquid ejected from the ejection port 56 collides with the collision surface 96 in the same manner as in the first embodiment. Thereby, in the hollow portion 46, a flow (arrow X1 in FIG. 24) is formed, by which at least part of the liquid ejected from the ejection port 56 flows toward the suction conduit 55 from the collision surface 96 through the suction port 57. Besides, part of the liquid ejected from the ejection port 56 does not collide with the collision surface 96, and is ejected to the outside of the probe 41 from the opening portion 47 (arrow X2 in FIG. 24).

In the present modification, liquid flows from the liquid feed conduit 53 into the suction conduit 55 through the communication portions 101A and 101B. Thus, the amount of liquid flowing in the suction conduit 55 toward the probe proximal portion direction increases. Thereby, the viscosity of the sucked object (crushed biological tissue or the like) lowers, and clogging less easily occurs in the suction conduit 55. In addition, at least part of the liquid supplied through the liquid feed conduit 53 is supplied to the ejection port 56, and is ejected from the ejection port 56 in the hollow portion 46. Then, at least part of the liquid jetted from the jet port 56 collides with the collision surface 96, and flows into the suction conduit 55 through the suction port 57. Thus, in the suction conduit 55, the liquid flows toward the probe proximal portion direction in the region between the suction port 57 and the communication portions 101A and 101B. Therefore, in the present modification, too, in which the communication portions 101A and 101B are provided, the occurrence of clogging can effectively be prevented in the region between the suction port 57 of the suction conduit 55 and the communication portions 101A and 101B.

Additionally, for example, also in a 14th modification illustrated in FIG. 25, communication portions 101A and 101B are provided for establishing communication between the liquid feed conduit 53 and suction conduit 55 on the probe proximal portion direction side with respect to the ejection port 56 and suction port 57. In this modification, like the first modification, the liquid feed tube 51 is inserted through the suction tube 52. In addition, the opening portions 47A and 47B are provided on the treatment section distal surface 92 at the same positions and with the same shapes as in the first modification (see FIG. 10 and FIG. 11).

In the present modification, like the 13th modification, part of the liquid supplied from the liquid feed actuation section 77 (liquid feed source 76) flows from the liquid feed conduit 53 into the suction conduit 55 through the communication portions 101A and 101B (arrow X3 in FIG. 25). However, at least part of the liquid supplied from the liquid feed actuation section 77 to the liquid feed conduit 53 does not flow into the suction conduit 55 from the communication portions 101A and 101B, and is supplied to the ejection port 56. Then, in the hollow portion 46, the liquid supplied to the ejection port 56 is ejected toward the probe distal portion direction side from the ejection port 56. At least part of the liquid ejected from the ejection port 56 collides with the collision surface 96 in the same manner as in the 13th modification. Thereby, in the hollow portion 46, a flow (arrow X1 in FIG. 25) is formed, by which at least part of the liquid ejected from the ejection port 56 flows toward the suction conduit 55 from the collision surface 96 through the suction port 57. Besides, part of the liquid ejected from the ejection port 56 does not collide with the collision surface 96, and is ejected to the outside of the probe 41 from the opening portions 47A and 47B (arrow X2 in FIG. 25).

In the meantime, also in the configuration in which only the suction tube 52 is provided, as in the eleventh modification illustrated in FIG. 22, the suction tube 52 may be provided with the communication portions (101A, 101B) for establishing communication between the liquid feed conduit 53 and suction conduit 55 on the probe proximal portion direction side with respect to the ejection port 56 and suction port 57. Besides, also in the configuration in which only the liquid feed tube 51 is provided, as in the twelfth modification illustrated in FIG. 23, the liquid feed tube 51 may be provided with the communication portions (101A, 101B) for establishing communication between the liquid feed conduit 53 and suction conduit 55 on the probe proximal portion direction side with respect to the ejection port 56 and suction port 57.

Additionally, in the above-described embodiment, etc., the collision surface 96 is provided in the probe distal wall 91 of the probe 41 (treatment section 42), but the restriction to this is unnecessary. For example, as illustrated in FIG. 26 as a 15th modification, a projection portion 102 projecting toward the inner peripheral side of the probe 41 may be provided on the probe proximal portion direction side with respect to the probe distal wall 91, and a collision surface 96 may be formed in the projection portion 102. In this modification, too, the collision surface 96 faces toward the probe proximal portion direction, and is opposed to at least a part of the ejection port 56 of the liquid feed conduit 53.

Additionally, in a 16th modification illustrated in FIG. 27, in the outside of the probe 41, an external liquid feed tube 103 may extend from the probe proximal portion direction toward the probe distal portion direction. An external liquid feed conduit 105 is formed in the inside of the external liquid feed tube 103. Accordingly, the external liquid feed conduit 105 extends from the probe proximal portion direction toward the probe distal portion direction through the outside of the probe 41. The distal end of the external liquid feed conduit 105 is formed by an external ejection port 107 which is located in the outside of the probe 41. In this modification, the external ejection port 107 is located on the probe-side counter-surface 95 of the treatment section side surface 93 of the treatment section 42. Accordingly, the external ejection port 107 is located on the probe distal portion direction side with respect to the distal end of the sheath 40.

The external liquid feed conduit 105 (external liquid feed tube 103) extends up to the inside of the holding unit 3 toward the probe proximal portion direction, through between the outer peripheral surface of the probe 41 and the inner peripheral surface of the sheath 40. In this modification, one end of an external liquid feed tube (not shown), which is different from the external liquid feed tube 73, can be connected to the holding unit 3. By the external liquid feed tube being connected to the holding unit 3, the proximal end (one end) of the external liquid feed conduit 105 communicates with the inside of the external liquid feed tube.

Additionally, in the present modification, a liquid feed source (not shown), which is different from the liquid feed source 76, is provided in the energy treatment system 1. The other end of the external liquid feed tube is connected to the liquid feed source. The liquid feed source, like the liquid feed source 76, is provided with a liquid feed actuation section (not shown) such as a liquid feed pump, and a liquid storage tank (not shown), and the actuation state of the liquid feed actuation section is controlled by the controller 18. By the liquid feed actuation section being actuated, a liquid, such as physiological saline, which is stored in the liquid storage tank, is supplied (fed) to the external liquid feed conduit 105 through the inside of the external liquid feed tube. In addition, in the external liquid feed conduit 105, the liquid is supplied from the probe proximal portion direction to the probe distal portion direction. Thereby, the supplied liquid is ejected from the external ejection port 107 toward the probe distal portion direction side, and the liquid is supplied to the vicinity of the treatment section distal surface 92.

In this modification, the external ejection port 107 is located on the probe-side counter-surface 95. Thus, by the jaw 43 being closed relative to the treatment section 42, the jet speed of the liquid, which is ejected from the external ejection port 107, increases. Therefore, the liquid supplied from the liquid feed source does not drop, for example, from the proximal portion of the treatment section 42 to a region other than the treatment target, and the liquid is properly supplied to the vicinity of the treatment section distal surface 92 in the outside of the probe 41.

In this modification, like the first embodiment, the suction tube 52 is inserted through the inside of the liquid feed tube 51. In addition, like the first embodiment, the opening portion 47 is provided on the treatment section distal surface 92. Accordingly, like the first embodiment, the collision surface 96, which is provided in the probe distal wall 91, is opposed to at least a part of the ejection port 56. By the above-described configuration, also in the present modification, in the hollow portion 46, at least part of the liquid, which was ejected from the ejection port 56, collides with the collision surface 96. Thereby, in the hollow portion 46, a flow (arrow X1 in FIG. 27) is formed, by which at least part of the liquid ejected from the ejection port 56 flows toward the suction conduit 55 from the collision surface 96 through the suction port 57. In addition, part of the liquid ejected from the ejection port 56 is ejected to the outside of the probe 41 from the hollow portion 46 through the opening portion 47 (arrow X2 in FIG. 27).

Additionally, in the above-described embodiment, etc., part of the liquid, which has been ejected from the ejection port 56 of the liquid feed conduit 53, is ejected from the opening portion (47; 47A, 47B; 47A to 47D; 97; 97A, 97B; 97A to 97D; 47, 97A, 97B; 47A, 47B, 97A, 97B) to the outside of the probe 41, and is supplied to the vicinity of the treatment section distal surface 92. However, the restriction to this is unnecessary. For example, in a 17th modification illustrated in FIG. 28, the liquid ejected from the ejection port 56 is not ejected to the outside of the probe 41. In this modification, like the 16th modification, in addition to the liquid feed conduit 53 which supplies liquid that is to be caused to flow into the suction conduit 55 from the suction port 57, there is provided an external liquid feed conduit 105 which supplies liquid, which is used for treatment, to the vicinity of the treatment section distal surface 92 in the outside of the probe 41. In this modification, all liquid ejected from the ejection port 56 collides with the collision surface 96. Thereby, in the hollow portion 46, a flow (arrow X1 in FIG. 28) is formed, by which all liquid ejected from the ejection port 56 flows toward the suction conduit 55 from the collision surface 96 through the suction port 57. By adjusting the supply amount of liquid to the ejection port 56 of the liquid feed conduit 53 by controlling the actuation state of the liquid feed actuation section 77, all liquid ejected from the ejection port 56 can be made to flow into the suction conduit 55 through the suction port 57.

In this modification, the liquid feed conduit 53 supplies only the liquid that is to be caused to flow into the suction conduit 55 from the suction port 57. In addition to the liquid feed conduit 53, the external liquid feed conduit 105 is provided which supplies liquid, which is used for treatment, to the vicinity of the treatment section distal surface 92 in the outside of the probe 41. Accordingly, by controlling the actuation state of the liquid feed actuation section 77 which supplies liquid to the liquid feed conduit 53 and by controlling the actuation state of the liquid feed actuation section (not shown) which supplies liquid to the external liquid feed conduit 105, it becomes possible to cause liquid to flow into the suction conduit 55 from the suction port 57, even in a treatment in which liquid (physiological saline) is not used. For example, when energy is output from the energy source unit 15 in the first output mode described in the first embodiment (i.e. when the probe 41 transmits ultrasonic vibration and the treatment section 42 and the electric conductor portion of the jaw 43 function as electrodes of high-frequency electric power), the liquid feed actuation section 77, which supplies liquid to the liquid feed conduit 53, is actuated, and the actuation of the liquid feed actuation section, which supplies liquid to the external liquid feed conduit 105, is stopped. Thereby, no liquid is ejected from the external ejection port 107, and all liquid ejected from the ejection port 56 collides with the collision surface 96 and flows into the suction conduit 55 through the suction port 57. Accordingly, the treatment performance of the treatment, which cuts the treated target while coagulating the treated target, does not deteriorate due to the liquid in the outside of the probe 41, and the occurrence of clogging in the suction conduit 55 is prevented.

Figure 29:
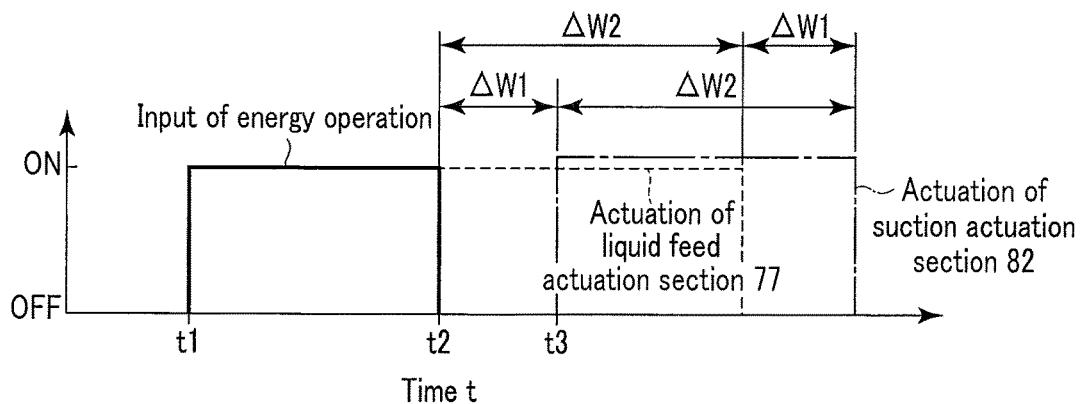
FIG. 29 is a schematic view illustrating an example of variations with time of the presence/absence of an input of an energy operation in an energy operation input section, an actuation state of a liquid feed actuation section, and an actuation state of a suction actuation section according to a 18th modification.

Additionally, in an 18th embodiment, the output state of energy from the energy source unit 15, the actuation state of the liquid feed actuation section 77 and the actuation state of the suction actuation section 82 are controlled by the controller 18, as illustrated in FIG. 29. FIG. 29 is a view illustrating an example of variations with time of the presence/absence of an input of an energy operation in the energy operation input section (9A to 9C, 10), the actuation state of the liquid feed actuation section 77, and the actuation state of the suction actuation section 82. In FIG. 29, a solid line indicates the variation of the input of the energy operation, a broken line indicates the variation of the actuation state of the liquid feed actuation section 77, and a dot-and-dash line indicates the variation of the actuation state of the suction actuation section 82.

In the example shown in FIG. 29, the energy operation in the energy operation input section (one of 9A to 9C, and 10) is input between time t1 and time t2 (an input ON state of an energy operation). When an energy operation was input by each energy operation input section (9A to 9C, 10), energy, which is used for treatment, is output from the energy source unit 15 in the output mode (one of the first output mode to fourth output mode) described in the first embodiment, and the actuation state of the liquid feed actuation section 77 and the actuation state of the suction actuation section 82 are controlled as described in the first embodiment. Then, if the input of the energy operation is stopped at time t2 (if the energy operation enters an input OFF state), the liquid feed actuation section 77 is automatically actuated at the same time, and liquid is supplied through the liquid feed conduit 53 (the liquid feed actuation section 77 enters an ON state). Then, at time t3 at which a predetermined time ΔW1 has passed since time t2 at which the actuation of the liquid feed actuation section 77 was started (i.e. at which the supply of liquid from the liquid feed source 76 was started), the suction actuation section 82 is automatically actuated (the suction actuation section 82 enters an ON state).

By the liquid feed actuation section 77 and suction actuation section 82 being actuated, at least part of the liquid ejected from the ejection port 56 collides with the collision surface 96 in the hollow portion 46, as described above. Thereby, in the hollow portion 46, a flow is formed, by which at least part of the liquid ejected from the ejection port 56 flows toward the suction conduit 55 from the collision surface 96 through the suction port 57. Then, the liquid feed actuation section 77 is stopped (the liquid feed actuation section 77 enters an OFF state) after a predetermined time ΔW2 has passed since time t2 (i.e. since the actuation of the liquid feed actuation section 77 was started). In addition, the suction actuation section 82 is stopped (the suction actuation section 82 enters an OFF state) after a predetermined time ΔW2 has passed since time t3 (i.e. since the actuation of the suction actuation section 82 was started). Thus, the actuation of the suction actuation section 82 is stopped after a predetermined time ΔW1 has passed since the actuation of the liquid feed actuation section 77 was stopped.

By the liquid feed actuation section 77 and suction actuation section 82 being controlled as described above, the occurrence of clogging in the suction conduit 55 can more effectively be prevented in the treatment using energy. In the meantime, even when the liquid feed operation or suction operation described in the first embodiment, in place of the energy operation, is input between time t1 and time t2, the actuation state of the liquid feed actuation section 77 and the actuation state of the suction actuation section 82 may be controlled with the passing of time, as described above in the present modification, after time t2 (i.e. after the input of the liquid feed operation or suction operation is stopped).

Additionally, in the above-described embodiment, etc., the treated target can be grasped between the jaw 43 and treatment section 42 by the energy treatment instrument 2, but the restriction to this is unnecessary. For example, in a certain modification, the jaw 43 may not be provided. In this case, the stationary handle 6, movable handle 7 and rotary operation knob 8 are not provided in the holding unit 3. In addition, the treatment, by which the treated target grasped between the jaw 43 and treatment section 42 is cut, while being coagulated, by ultrasonic vibration, is not performed. However, in this case, too, the probe 41 transmits ultrasonic vibration as energy which is used for treatment. In addition, in the treatment section 42 (in the vicinity of the treatment section distal surface 92), the treated target is crushed and emulsified by cavitation, as described above, and the crushed and emulsified treated target is sucked through the suction conduit 55.

Additionally, in a certain modification, the probe 41 may not transmit ultrasonic vibration, and only high-frequency electric power may be supplied as energy to the treatment section 42 through the probe 41. In this case, by the high-frequency electric power being supplied to the treatment section 42, a high-frequency current is passed through the treated target, and the treated target is resected by the high-frequency current. Then, the resected treated target is sucked through the suction conduit 55 which extends through the hollow portion 46 of the probe 41.

Additionally, in a certain modification, a heat generation body (not shown) such as a thermocouple may be provided in the treatment section 42, and electric power may be supplied to the heat generation body through the probe 41. By the electric power being supplied as energy, heat, which is used in treatment, is generated in the heat generation body. Then, using the generated heat, the treated target is resected, and the resected treated target is sucked through the suction conduit 55 which extends in the hollow portion 46 of the probe 41.

Additionally, in a certain modification, the treatment section 42 (probe distal portion) of the probe 41 may be provided with a probe bend portion which bends in a certain direction crossing the straight longitudinal axis C. In this case, too, like the above-described embodiment, etc., the liquid feed conduit 53 and suction conduit 55 extend in the hollow portion 46 in the inside of the probe 41, and the collision surface 96 is formed in the probe 41.

In the above-described embodiment, etc., the probe (41) extends along the longitudinal axis (C), and can transmit energy. In addition, the probe (41) includes, in the distal portion thereof, the treatment section (42) which performs treatment by using the transmitted energy, and the hollow portion (46) is formed along the longitudinal axis (C) in the inside of the probe (41). The hollow portion (46) is open to the outside of the probe (41) at the opening portion (47; 47A, 47B; 47A to 47D; 97; 97A, 97B; 97A to 97D; 47, 97A, 97B; 47A, 47B, 97A, 97B) on the outer surface of the treatment section (42). In addition, in the hollow portion (46), the liquid feed conduit (53) and suction conduit (55) extend from the probe proximal portion direction to the probe distal portion direction. The distal end of the suction conduit (55) is formed by the suction port (57) which is located in the hollow portion (46), and the distal end of the liquid feed conduit (53) is formed by the ejection port (56) which is located in the hollow portion (46). By a flow occurring toward the probe proximal portion direction in the suction conduit (55), suction force acts from the outside of the probe (41) toward the suction conduit (55) through the opening portion (47; 47A, 47B; 47A to 47D; 97; 97A, 97B; 97A to 97D; 47, 97A, 97B; 47A, 47B, 97A, 97B) of the hollow portion (46) and the suction port (57). In addition, by liquid being supplied toward the probe distal portion direction in the liquid feed conduit (53), the supplied liquid in the hollow portion (46) is ejected from the ejection port (56) toward the probe distal portion direction side. In the probe (41), the collision surface (96) is provided in such a state that the collision surface (96) is opposed to at least a part of the ejection port (56). The collision surface (96) is located on the probe distal portion direction side with respect to the suction port (57) and jet port (56). In the hollow portion (46), at least part of the liquid ejected from the ejection port (56) collides with the collision surface (96), and the direction of the flow of the liquid, which collides with the collision surface (96), is changed. Thereby, in the hollow portion (46), a flow of liquid is formed toward the suction conduit (55) from the collision surface (96) through the suction port (57).

If the above-described configuration is satisfied, proper changes can be made to the number and shape of opening portions (47; 47A, 47B; 47A to 47D; 97; 97A, 97B; 97A to 97D; 47, 97A, 97B; 47A, 47B, 97A, 97B), and to the states of extending of the liquid feed conduit (53) and suction conduit (55) in the hollow portion (46).

REFERENCE EXAMPLE

Figure 30:
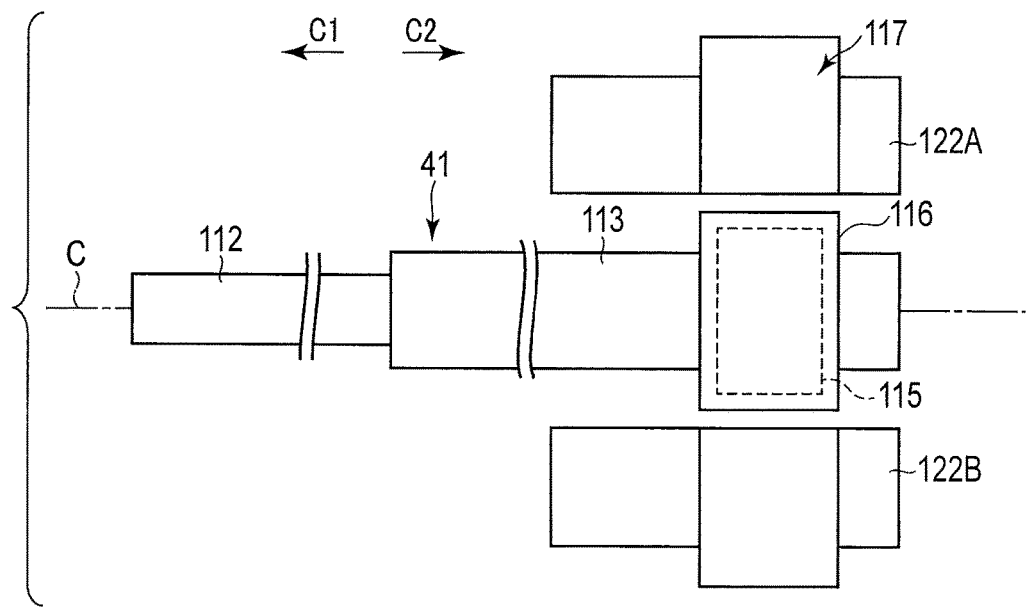
FIG. 30 is a schematic view illustrating the configuration of a probe and a probe holder, to which the probe is fixed, according to a reference example.
Figure 31:
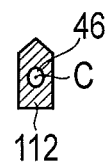
FIG. 31 is a cross-sectional view which schematically illustrates a cross section perpendicular to a longitudinal axis of a treatment section according to the reference example.

Hereinafter, a reference example will be described with reference to FIG. 30 to FIG. 32. FIG. 30 is a view illustrating the configuration of a probe 41 and a probe holder 117 to which the probe 41 is fixed. As illustrated in FIG. 30, in the reference example, the probe 41 includes a distal-side probe 112 and a proximal-side probe 113 which is connected to a probe proximal portion direction side of the distal-side probe 112. Time and labor is required for a process of forming a hole which penetrates an elongated columnar member in the longitudinal direction. Thus, by connecting two members (e.g. the distal-side probe 112 and proximal-side probe 113) by screwing or the like, time and labor for manufacturing the probe 41 is reduced even when a hollow portion 46 penetrating the probe 41 along the longitudinal axis C is formed in the inside of the probe 41.

In this reference example, the distal-side probe 112 is provided with a treatment section 42. FIG. 31 illustrates a cross section perpendicular to the longitudinal axis C of the treatment section 42. As illustrated in FIG. 31, in the cross section perpendicular to the longitudinal axis C of the treatment section 42, the shape surrounded by the outer surface (treatment section side surface 93) is substantially pentagonal, and is not point-symmetric (non-point symmetric) with respect to the longitudinal axis C.

In addition, the proximal-side probe 113 is provided with a flange portion 115. A probe stopper member 116 is fixed to the flange portion 115. Furthermore, the sheath 40 is provided with a probe holder 117. By the probe stopper member 116 being fixed to the probe holder 117, the probe 41 is attached to the sheath 40.

Figure 32:
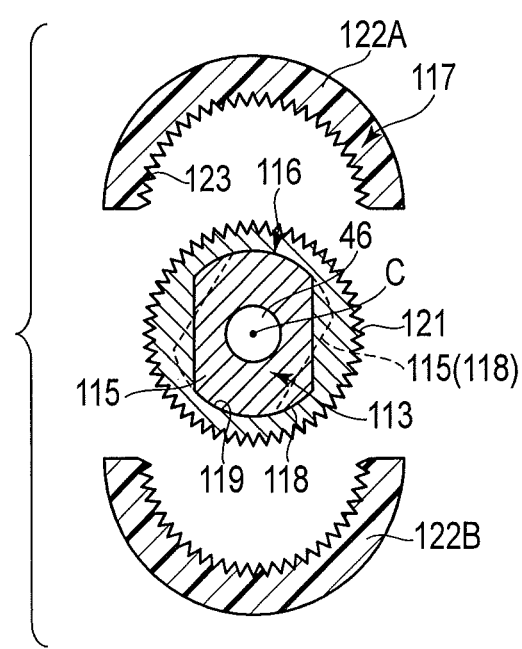
FIG. 32 is a cross-sectional view which schematically illustrates a cross section perpendicular to a longitudinal axis passing through a flange portion of the probe and the probe holder according to the reference example.

FIG. 32 illustrates a cross section perpendicular to the longitudinal axis C passing through the flange portion 115 of the probe 41 and the probe holder 117. As illustrated in FIG. 32, in the probe 41 (proximal-side probe 113), an engaging outer peripheral surface 118 is formed by an outer peripheral surface of the flange portion 115. In the cross section perpendicular to the longitudinal axis C, the shape surrounded by the engaging outer peripheral surface 118 of the flange portion 115 is not point-symmetric (non-point symmetric) with respect to the longitudinal axis C. Specifically, the engaging outer peripheral surface 118 of the flange portion 115 is formed non-point symmetric with respect to the longitudinal axis C.

In the probe 41 in which the proximal-side probe 113 is connected to the distal-side probe 112, the angular position around the longitudinal axis C of the engaging outer peripheral surface 118 (flange portion 115), relative to the treatment section 42, varies from product to product. For example, in a certain probe 41, relative to the treatment section 42 disposed at an angular position shown in FIG. 31 around the longitudinal axis C, the engaging outer peripheral surface 118 is disposed at an angular position around the longitudinal axis C, which is indicated by a solid line in FIG. 32. However, in another probe 41, relative to the treatment section 42 disposed at the angular position shown in FIG. 31 around the longitudinal axis C, the flange portion 115 is disposed at an angular position around the longitudinal axis C, which is indicated by a broken line in FIG. 32.

In addition, an engaging inner peripheral surface 119, which is engaged with the engaging outer peripheral surface 118, is formed by an inner peripheral surface of the probe stopper member 116. By the engaging inner peripheral surface 119 being engaged with the engaging outer peripheral surface 118, the probe stopper member 116 is fixed to the probe 41 (proximal-side probe 113). In the cross section perpendicular to the longitudinal axis C, the engaging inner peripheral surface 119 is formed to have a shape corresponding to the engaging outer peripheral surface 118 (a shape engageable with the engaging outer peripheral surface 118). Thus, in the cross section perpendicular to the longitudinal axis C, the shape surrounded by the engaging inner peripheral surface 119 of the probe stopper member 116 is not point-symmetric (non-point symmetric) with respect to the longitudinal axis C. Specifically, the engaging inner peripheral surface 119 of the probe stopper member 116 is formed non-point symmetric with respect to the longitudinal axis C.

When the probe stopper member 116 is fixed to the flange portion 115 of the probe 41, the angular position around the longitudinal axis C of the engaging inner peripheral surface 119 is adjusted in such a state as to be engageable with the engaging outer peripheral surface 118, in accordance with the angular position around the longitudinal axis C of the engaging outer peripheral surface 118. In addition, as described above, the angular position around the longitudinal axis C of the engaging outer peripheral surface 118 (flange portion 115), relative to the treatment section 42, varies from product to product. Accordingly, the angular position around the longitudinal axis C of the engaging inner peripheral surface 119, relative to the treatment section 42, varies from product to product.

Additionally, a projection-and-recess outer peripheral surface 121 is formed on the outer peripheral surface of the probe stopper member 116 over the entire circumference around the longitudinal axis C. In the cross section perpendicular to the longitudinal axis C, the shape surrounded by the projection-and-recess outer peripheral surface 121 of the probe stopper member 116 is point-symmetric with respect to the longitudinal axis C. Specifically, the projection-and-recess outer peripheral surface 121 of the probe stopper member 116 is formed point-symmetric with respect to the longitudinal axis C. Thus, even if the angular position around the longitudinal axis C of the engaging inner peripheral surface 119 (probe stopper member 116) varies, the cross-sectional shape perpendicular to the longitudinal axis C of the projection-and-recess outer peripheral surface 121 does not change.

The probe holder 117 includes holder forming members 122A and 122B. In addition, a projection-and-recess inner peripheral surface 123 is formed on the inner peripheral surface of the probe holder 117 over the entire circumference around the longitudinal axis C. In the cross section perpendicular to the longitudinal axis C, the projection-and-recess inner peripheral surface 123 is formed to have a shape corresponding to the projection-and-recess outer peripheral surface 121 (a shape engageable with the projection-and-recess outer peripheral surface 121). Thus, in the cross section perpendicular to the longitudinal axis C, the shape surrounded by the projection-and-recess inner peripheral surface 123 of the probe holder 117 is point-symmetric with respect to the longitudinal axis C. Specifically, the projection-and-recess inner peripheral surface 123 of the probe holder 117 is formed point symmetric with respect to the longitudinal axis C.

In this reference example, the projection-and-recess outer peripheral surface 121 and projection-and-recess inner peripheral surface 123 are point-symmetric with respect to the longitudinal axis C. Thus, by attaching the holding forming members 122A and 122B to the probe stopper member 116, the projection-and-recess inner peripheral surface 123 is engaged with the projection-and-recess outer peripheral surface 121, regardless of the angular position around the longitudinal axis C of the engaging inner peripheral surface 119 (probe stopper member 116). Specifically, the probe holder 117 is fixed to the probe stopper member 116, without adjusting the angular position around the longitudinal axis C of the projection-and-recess inner peripheral surface 123 relative to the projection-and-recess outer peripheral surface 121.

Because of the above-described configuration, when the probe 41 is attached to the probe holder 117 (sheath 40), the engaging inner peripheral surface 119 of the probe stopper member 116 is engaged with the engaging outer peripheral surface 118 of the flange portion 115, in the state in which the treatment section 42 is disposed at a predetermined angular position around the longitudinal axis C. At this time, although the angular positions around the longitudinal axis C of the engaging outer peripheral surface 118 and engaging inner peripheral surface 119 vary from product to product, the projection-and-recess inner peripheral surface 123 is engaged with the projection-and-recess outer peripheral surface 121, regardless of the angular position around the longitudinal axis C of the engaging inner peripheral surface 119 (probe stopper member 116). Thus, even when the angular positions around the longitudinal axis C of the engaging outer peripheral surface 118 and engaging inner peripheral surface 119 vary from product to product, the probe holder 117 can easily be fixed to the probe stopper member 116.

Additionally, in this reference example, there is no need to process the probe stopper member 116 in accordance with the angular position about the longitudinal axis C of the probe stopper member 116 (flange position 115), in the state in which the probe stopper member 116 is fixed to the probe 41. For example, in the configuration in which the probe holder (117) is fixed to the probe stopper member (116) by a fixing screw, it is necessary to form a screw hole in the probe stopper member (116) in accordance with the angular position around the longitudinal axis C of the probe stopper member (116), in the state in which the probe stopper member (116) is fixed to the probe (41). However, in this reference example, there is no need to form this screw hole. Accordingly, the probe 41 can easily be attached (fixed) to the probe holder 117 (sheath 40) in the state in which the treatment section 42 is disposed at a predetermined angular position around the longitudinal axis C.

Additionally, the projection-and-recess outer peripheral surface 121 of the probe stopper member 116 and the projection-and-recess inner peripheral surface 123 of the probe holder 117 are engaged over the entire circumference around the longitudinal axis C. Thus, the probe 41 can firmly be fixed to the probe holder 117. Therefore, the strength of the probe 41 and probe holder 117 can be secured.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment apparatus for use with biological tissue, the energy treatment apparatus comprising:
   a probe extending along a longitudinal axis from a probe distal portion to a probe proximal portion, the probe having a treatment section configured to treat biological tissue by using energy transmitted from the probe proximal portion toward the probe distal portion;
   a hollow portion having an opening portion opened with respect to an exterior of the probe, the hollow portion being provided in an interior of the probe along the longitudinal axis;
   a suction conduit extending in an interior of the hollow portion from the probe proximal portion to the probe distal portion, and including a distal end at which a suction port located in the hollow portion is formed, the suction conduit being configured such that suction force occurs from the suction port toward the probe proximal portion;
   a liquid feed conduit extending in the interior of the hollow portion from the probe proximal portion to the probe distal portion, and including a distal end at which an ejection port located in the hollow portion is formed, the liquid feed conduit being configured to eject liquid from the ejection port toward a side of the probe distal portion; and
   a collision surface located on the side of the probe distal portion with respect to the suction port and the ejection port, the collision surface and the probe being formed as a unitary structure such that the collision surface is located on an inner surface of the probe, the inner surface of the probe forming a peripheral surface of the hollow portion, the collision surface being opposed to at least part of the ejection port so that:
   (i) the collision surface changes a flowing direction of a part of the liquid, which has been ejected from the ejection port toward the opening portion in the hollow portion, to a direction toward the probe proximal portion, and
   (ii) the collision surface makes another part of the liquid, which has been ejected from the ejection port, ejected towards the exterior of the probe through the opening portion.

2. The energy treatment unit of claim 1, further comprising:
   a communication portion configured to establish communication between the liquid feed conduit and the suction conduit on a side of the probe proximal portion with respect to the suction port and the ejection port, wherein
   at least part of the liquid, which passes through the liquid feed conduit, does not flow into the suction conduit from the communication portion, and is supplied to the ejection port.

3. The energy treatment unit of claim 1, wherein
   a cross section of the suction conduit, which is perpendicular to the longitudinal axis, has a cylindrical shape surrounding an outer peripheral side of the liquid feed conduit, and
   the ejection port of the liquid feed conduit is located on the side of the probe distal portion with respect to the suction port of the suction conduit.

4. The energy treatment unit of claim 1, wherein
   a cross section of the liquid feed conduit, which is perpendicular to the longitudinal axis, has a cylindrical shape surrounding an outer peripheral side of the suction conduit, and
   the suction port of the suction conduit is located on the side of the probe distal portion with respect to the ejection port of the liquid feed conduit.

5. The energy treatment unit of claim 1, wherein
   the probe is configured to transmit ultrasonic vibration from the probe proximal portion to the probe distal portion, and
   the collision surface is configured to vibrate integrally with the probe when the probe transmits the ultrasonic vibration.

6. The energy treatment unit of claim 1, wherein the opening portion of the hollow portion and the collision surface are formed in the treatment section provided in the probe distal portion.

7. The energy treatment unit of claim 6, wherein
the treatment section includes a treatment section distal surface, and a treatment section side surface extending from the treatment section distal surface toward the probe proximal portion direction, and
the opening portion of the hollow portion and the collision surface are formed on the treatment section distal surface.

8. The energy treatment unit of claim 1, wherein the ejection port of the liquid feed conduit is located at the same position as the suction port of the suction conduit in a longitudinal axis direction, or located on the probe proximal portion direction side with respect to the suction port.

9. The energy treatment unit of claim 8, wherein the opening portion of the hollow portion is located at the same position as the suction port of the suction conduit in the longitudinal axis direction, or located on the probe distal portion direction side with respect to the suction port.

10. The energy treatment unit of claim 1, wherein the probe, the liquid feed conduit and the suction conduit are coaxial with one another.

11. The energy treatment unit of claim 1, further comprising:
a relay member; and
a tube fixing member fastened to the relay member in a threaded manner, wherein
a fastening degree between the tube fixing member and the relay member is adjusted so that positions of the ejection port of the liquid feed conduit and the suction port of the suction conduit are adjusted.

12. The energy treatment unit of claim 1, wherein
an outer surface of the treatment section includes a treatment section distal surface which forms a distal end of the probe, and a treatment section side surface extending from the treatment section distal surface toward the probe proximal portion direction, and
the opening portion of the hollow portion is located on the treatment section side surface or the treatment section distal surface.

13. The energy treatment unit of claim 12, wherein
the opening portion is a plurality of opening portions formed on the treatment section side surface,
in a first opening portion which is one of the opening portions, a distance from the suction port of the suction conduit is less than a distance from the ejection port of the liquid feed conduit, and
in a second opening portion which is another of the opening portions and is different from the first opening portion, a distance from the ejection port of the liquid feed conduit is less than a distance from the suction port of the suction conduit.

14. The energy treatment unit of claim 12, wherein
when the opening portion of the hollow portion is located on the treatment section distal surface:
a position of the ejection portion of the liquid feed conduit is located on a side of the probe proximal portion with respect to the opening portion, and
a position of the suction port of the suction conduit is located on the side of the probe proximal portion with respect to the opening portion.

15. An energy treatment instrument comprising:
the energy treatment unit of claim 12;

a sheath through which the probe is inserted in a state in which the treatment section projects toward the side of the probe distal portion; and
a jaw rotatably attached to the sheath, and configured to rotate relative to the sheath, thereby opening or closing relative to the treatment section of the probe, wherein
the treatment section side surface of the treatment section includes a probe-side counter-surface which is opposed to the jaw, and which faces toward an opening direction of the jaw, and
the opening portion of the hollow portion is located at a position on the treatment section side surface of the treatment section, which is other than the probe-side counter-surface.

16. An energy treatment instrument comprising:
the energy treatment unit of claim 1;
a sheath through which the probe is inserted in a state in which the treatment section projects toward the side of the probe distal portion direction; and
a holding unit coupled to the sheath from a side of the probe proximal portion of the sheath, and configured such that the probe extends from an inside of the holding unit toward the probe distal portion through an inside of the sheath.

17. The energy treatment instrument of claim 16, further comprising:
a conduit attachment/detachment portion configured to detachably couple the liquid feed conduit and the suction conduit to the probe and the holding unit, by inserting, in the inside of the holding unit, the liquid feed conduit and the suction conduit from the side of the probe proximal portion into the hollow portion of the probe.

18. An energy treatment instrument comprising:
the energy treatment unit of claim 1;
an external liquid feed conduit extending from a side of the probe proximal portion toward the side of the probe distal portion through the outside of the probe, the external liquid feed conduit including a distal end at which an external ejection port located on the outside of the probe is formed, and the external liquid feed conduit being configured to eject supplied liquid from the external ejection port toward the side of the probe distal portion;
a sheath through which the probe is inserted in a state in which the treatment section projects toward the side of the probe distal portion; and
a jaw rotatably attached to the sheath, and configured to rotate relative to the sheath, thereby opening or closing relative to the treatment section of the probe, wherein
an outer surface of the treatment section includes a probe-side counter-surface which is opposed to the jaw, and which faces toward an opening direction of the jaw,
the external liquid feed conduit extends through between the probe and the sheath, and
the external ejection port of the external liquid feed conduit is located on the side of the probe distal portion with respect to a distal end of the sheath, and is located on the probe-side counter-surface.

19. An energy treatment system comprising:
the energy treatment unit of claim 1; and
an energy source unit configured to output the energy which is used for the treatment in the treatment section, the output energy being transmitted to the treatment section through the probe.

20. The energy treatment system of claim 19, further comprising:

a vibration causing section configured to cause ultrasonic vibration by being supplied with electric power, wherein the energy source unit includes an ultrasonic energy source configured to output, as the energy, electric power which is supplied to the vibration causing section, the probe is configured to transmit the ultrasonic vibration, which is caused by the ultrasonic causing section, from the probe proximal portion to the probe distal portion, and the treatment section is configured to perform the treatment by using the transmitted ultrasonic vibration.

21. The energy treatment system of claim 20, wherein the liquid feed conduit and the suction conduit extend from the probe proximal portion direction toward the probe distal portion direction through a cavity portion, the cavity portion being formed inside the vibration causing section.

* * * * *